United States Patent
Rima et al.

(10) Patent No.: US 8,048,317 B2
(45) Date of Patent: Nov. 1, 2011

(54) GENERATION OF FREE RADICALS, ANALYTICAL METHODS, BACTERIAL DISINFECTIONS, AND OXIDATIVE DESTRUCTION OF ORGANIC CHEMICALS USING ZERO VALENT IRON AND OTHER METALS

(75) Inventors: Jamil Rima, Beirut (LB); Qing X. Li, Honolulu, HI (US); Lizette Aouezova, Beirut (LB)

(73) Assignee: University of Hawaii, Honolulu, HI (US)

( * ) Notice: Subject to any disclaimer, the term of this patent is extended or adjusted under 35 U.S.C. 154(b) by 276 days.

(21) Appl. No.: 11/301,627

(22) Filed: Dec. 13, 2005

(65) Prior Publication Data

US 2006/0175266 A1  Aug. 10, 2006

Related U.S. Application Data

(60) Provisional application No. 60/636,018, filed on Dec. 13, 2004.

(51) Int. Cl.
*C02F 1/72* (2006.01)

(52) U.S. Cl. ........ 210/763; 210/764; 210/908; 210/909; 422/28; 424/646

(58) Field of Classification Search .................... 210/764
See application file for complete search history.

(56) References Cited

U.S. PATENT DOCUMENTS

| | | | |
|---|---|---|---|
| 3,640,821 A | 2/1972 | Sweeny et al. | |
| 4,382,865 A | 5/1983 | Sweeny | |
| 5,149,437 A * | 9/1992 | Wilkinson et al. | 210/665 |
| 5,178,768 A * | 1/1993 | White, Jr. | 210/663 |
| 5,198,118 A * | 3/1993 | Heskett | 210/638 |
| 5,266,213 A | 11/1993 | Gillham | |
| 5,352,369 A | 10/1994 | Heinig, Jr. et al. | |
| 5,534,154 A | 7/1996 | Gillham | |
| 5,616,253 A * | 4/1997 | Fernando et al. | 210/747 |
| 5,935,609 A * | 8/1999 | Denkewicz et al. | 424/618 |
| 5,975,798 A * | 11/1999 | Liskowitz et al. | 405/128.5 |
| 5,975,800 A * | 11/1999 | Edwards et al. | 405/128.15 |
| 6,207,073 B1 * | 3/2001 | Wolfe et al. | 252/175 |
| 6,221,262 B1 | 4/2001 | MacDonald et al. | |
| 6,306,641 B1 | 10/2001 | Horn et al. | |
| 6,787,034 B2 * | 9/2004 | Noland et al. | 210/610 |
| 6,942,807 B1 * | 9/2005 | Meng et al. | 210/719 |

(Continued)

FOREIGN PATENT DOCUMENTS

WO  WO 2005/028378 A1   3/2005

(Continued)

OTHER PUBLICATIONS

Alfaro, G., et al., *Liquid Analysis by Dry-Extract Near-Infrared Reflectance on Fiberglass*, Appl. Spectrosc., (1990) vol. 44, pp. 979-986.

(Continued)

*Primary Examiner* — Peter A Hruskoci
(74) *Attorney, Agent, or Firm* — Knobbe, Martens, Olson & Bear, LLP

(57) ABSTRACT

Disclosed are methods for chemical analysis, bacterial disinfection, oxidative destruction and/or mineralization of organic compounds comprising using zero-valent iron and/or zero-valent iron-containing bimetallic compounds, preferably in acidic solution and/or in the presence of oxygen.

12 Claims, 17 Drawing Sheets

U.S. PATENT DOCUMENTS

| | | | | |
|---|---|---|---|---|
| 7,008,964 | B2* | 3/2006 | Clausen et al. | 516/20 |
| 7,128,841 | B2* | 10/2006 | Zhang | 210/747 |
| 7,507,345 | B2* | 3/2009 | Zhang | 210/763 |
| 7,897,049 | B2* | 3/2011 | Ghosh et al. | 210/631 |
| 2003/0173306 | A1 | 9/2003 | Cha et al. | |
| 2003/0196966 | A1 | 10/2003 | Hughes | |
| 2006/0249465 | A1* | 11/2006 | Jin et al. | 210/764 |
| 2007/0256713 | A1* | 11/2007 | Feitz et al. | 134/42 |

FOREIGN PATENT DOCUMENTS

WO     WO 2005/053797 A1     6/2005

OTHER PUBLICATIONS

Arya, S., *Colorimetric Determination of Ascorbic Acid in Pharmaceutical Preparations and Biological Samples*, Mikrochim. Acta, (1997) vol. 127, pp. 45-49.

Barbeni, et al., *Chemical Degradation of Chlorophenols with Fenton's Reagent*, Chemosphere (1987) vol. 16, Nos. 10-12, pp. 2225-2237.

Bergendahl, et al., *Fenton's oxidation of MTBE with zero-valent iron*, Water Research 38 (2004), pp. 327-334.

Bowers, et al., *Treatment of Toxic or Refractory Wastewaters with Hydrogen Peroxide*. Wat. Sci. Tech. (1989) vol. 21, Brighton, pp. 477-486.

Burbano, et al., *Oxidation kinetics and effect of pH on the degradation of MTBE with Fenton reagent*, Water Research 39 (2005), pp. 107-118.

Cabrera, et al., *Acid Mine-Water and Agricultural Pollution in a River Skirting the Donana National Park (Guadiamar River. South West Spain)*, Water Res. (1984), vol. 18, No. 12, pp. 1469-1482.

Cheeseman, K., et al., *An Introduction to Free Radical Biochemistry*, Br. Med. Bull., (1993), vol. 29, No. 3, pp. 481-493.

Cheng I., et al., *Electrochemical Dechlorination of 4-Chlorophenol to Phenol*, Environ. Sci. Technol, (1997), vol. 31, pp. 1074-1078.

Deutsch, et al., *Ascorbate and Dehydroascorbate Measurements in Aqueous Solutions and Plasma Determined by Gas Chromatography-Mass Spectrometry*, Anal. Chem., (1993), vol. 65, pp. 321-326.

Deutsch, et al., *Variation in Ascorbic Acid Oxidation Routes in H2O2 and Cupric Ion Solution as Determined by GC/MS*, Anal. Chem. (1994), vol. 66, pp. 345-350.

Deutsch, et al., *Microfluorometric Assay for Vitamin C*, Journal of the A.O.A.C., (1965), vol. 48, No. 6, pp. 1248-1256.

Dong, C., *Destruction of Hazardous Organic Contaminants by Advanced Oxidation Processes*, A dissertation submitted to the Faculty of the University of Delaware, (Summer 1993), pp. 1-232.

Ferreira, et al., *Sensitive Spectrophotometric Determination of Ascorbic Acid in Fruit Juices and Pharmaceutical Formulations Using 2-(5-Bromo-2-Pyridylazo)-5-Diethylaminophenol (Br-PADAP)*, (1997), Fresenius J. Anal. Chem., vol. 357, pp. 1174-1178.

Fleming, et al., *Integrated Zero-Valent Iron and Dark Oxidation Processes for In-Situ Remediation of Explosives in Groundwater*, U.S. Army Engineer Research and Development Center, Waterways Experiment Station.

Frei, et al., *Ascorbate is an Outstanding Antioxidant in Human Blood Plasma*, Proc. Natl. Acad. Sci. USA, (1989), vol. 86, pp. 6377-6381.

Fridovich, Irwin, *Superoxide Radical: An Endogenous Toxicant*, Ann. Rev. Pharmacol. Toxicol.

Ghauch, A., et al., *Rapid Treatment of Water Contaminated with Atrazine and Parathion with Zero-Valent Iron*, Chemosphere, (1999), vol. 39, No. 8, pp. 1309-1315.

Ghauch, A., *Degradation of Benomyl, Picloram, and Dicamba in a Conical Apparatus by Zero-Valent Iron Powder*, Chemosphere (2004), vol. 43, pp. 1109-1117.

Gauch, A., et al., *Reductive Degradation of Carbaryl in Water by Zero-Valent Iron*, Chemosphere (2001), vol. 42, pp. 419-424.

Gharsallah, N., *Production of Single Cell Protein From Olive Mill Wastewater by Yeasts*, Environmental Technology, (1993), vol. 14, pp. 391-395.

Giangiacomo, et al., *Near Infrared Spectrophotometric Determination of Individual Sugars in Aqueous Mixtures*, Journal of Food Science, (1986), vol. 51, No. 3, pp. 679-683.

Gutteridge, J, *Reactivity of Hydroxyl and Hydroxyl-Like Radicals Discriminated by Release of Thiobarbituric Acid-Reactive Material from Deoxy Sugars. Nucleosides and Benzoate*, Biochem. J., (1984), vol. 224., pp. 761-767.

Hall, et al., *Mechanochemical Reaction of DDT with Calcium Oxide*, Environ. Sci., (1996), vol. 30, No. 12, pp. 3401-3407.

Hamdi, et al., *Future Prospects and Constraints of Olive Mill Wastewaters Use and Treatment: A Review*, Bioprocess Engineering, (1993), vol. 8, pp. 209-214.

Joo, et al., *Oxidative Degradation of the Carbothioate Herbicide, Molinate, Using Nanoscale Zero-Valent Iron*, Environ. Sci. Technol. (2004) vol. 38, pp. 2242-2247.

Joo, et al., *Quantification of the Oxidizing Capacity of Nanoparticulate Zero-Valent Iron*, Environ. Sci. Technol. (2005), vol. 39, pp. 1263-1268.

Kanel, et al., *Removal of Arsenic(III) from Groundwater by Nanoscale Zero-Valent Iron*, Environ. Sci. Technol., (2005), vol. 39, pp. 1291-1298.

Kim, Hie-Joon, *Determination of Total Vitamin C by Ion Exclusion Chromatography with Electrochemical Detection*, (1989), Anal. Chem., vol. 72, pp. 681-686.

Kishida, et al., *Specific Determination of Ascorbic Acid with Chemical Derivatization and High-Performance Liquid Chromatography*, Anal. Chem., (1992), vol. 64, pp. 1505-1507.

Kissinger, et al., *Determination of Ascorbic Acid and Dehydroascorbic Acid Using Liquid Chromatography with Ultraviolet and Electrochemical Detection*, Food Technology, (1987), pp. 108-111.

Kosugi, et al., *Formation of Yellow, Orange, and Red Pigments in the Reaction of Alk-2-enals with 2-Thiobarbituric Acid*, Analytical Biochemistry, (1987), vol. 165, pp. 456-464.

Lanza, et al., *Application for Near Infrared Spectroscopy for Predicting the Sugar Content of Fruit Juices*, Journal of Food Science, (1984), vol. 49, pp. 995-998.

Lau, et al., *Background Correction Method for the Determination of Ascorbic Acid in Soft Drinks. Fruit Juices and Cordials Using Direct Ultraviolet Spectrophotometry*, Analyst, (1986), vol. 111, pp. 665-670.

Li, et al., *Quantitative Analysis of Individual Sugars and Acids in Orange Juices by Near-Infrared Spectroscopy of Dry Extract*, J. Agric. Food Chem., (1996), vol. 44, pp. 2252-2259.

Lima de Souza, C., *Degradation of Reactive Corantes for the System Metallic Iron/Hydrogen Peroxide*, Quim. New (2005), vol. 28 in the, 2 Sao Paulo Sea.

Lobry De Bryuyn, et al., *Contributions a la Connaissance Des Corps Aromatiques Nitres*, (1985), Amsterdam, pp. 150-155.

Martin, et al., *Kinetic Study of an Anaerobic Fluidized Bed System Used for the Purification of Fermented Olive Mill Wastewater*, J. Chem. Tech., (1993), vol. 56, pp. 155-162.

Martin-Fernandez, et al., *Subnanosecod Polarized Microfluorimetry in the Time Domain: An Instrument for Studying Receptor Trafficking in Live Cells*, Review of Scientific Instruments, (1998), vol. 69, No. 2, pp. 540-543.

Matheson, et al., *Reductive Dehalogenation of Chlorinated Methanes by Iron Metal*, Eviron. Sci. Technol., (1994), vol. 28, pp. 2045-2053.

Morales, et al., *Hydrogenation of Phenol by the Pd/Mg and Pd/Fe Bimetallic Systems under Mild Reaction Conditions*, Ind. Eng. Chem. Res. (2002), vol. 41, pp. 3071-3074.

Mukhopadhyay, et al., *NADPH-Initiated Cytochrome P450-mediated Free Metal Ion-independent Oxidative Damage of Microsomal Proteins*, The Journal of Biological Chemistry, (1994), vol. 269, No. 18, pp. 13390-13397.

Mukhopadhyay, et al., *Ascorbic Acid Prevents Lipid Peroxidation and Oxidative Damage of Proteins in Guinea Pig Extrahepatic Tissue Microsomes*, Molecular and Cellular Biochemistry, (1995), vol. 142, pp. 71-78.

McClure, et al., *Two-Dimensional Correlation of Fourier Transform Near-Infrared and Fourier Transform Raman Spectra I: Mixtures of Sugar and Protein*, Applied Spectroscopy, (1996), vol. 50, pp. 467-475.

Pachla, et al., *Analytical Methods for Determining Ascorbic Acid in Biological Samples, Food Products, and Pharmaceuticals*, J. Assoc. Off. Anal. Chem., (1985), vol. 68, No. 1, pp. 1-12.

Sanjust, et al., *Olive Milling Wastewater as a Medium for Growth of Four Pleurotus Species*, Applied Biochemistry and Biotechnology, (1991), vol. 31, pp. 223-235.

Sayles, et al., *DDT, DDD, and DDE Dechlorination by Zero-Valent Iron*, Environ. Sci. Technol., (1997), vol. 31, pp. 3448-3454.

Slater, T, *Free-Radical Mechanisms in Tissue Injury*, Biochem J. (1984), vol. 222, pp. 1-15.

Sultan, et al., *Flow Injection of Colorimetric Method for the Assay of Vitamin C in Drug Formulations Using Tris, 1-10-Phenanthroline-Iron(III) Complex as an oxidant in Sulfuric Acid Media*, Talanta, (1994), vol. 41, No. 1, pp. 125-130.

Trifiro, et al., *Use of Iron Chromatography for Monitoring Microbial Spoilage in the Fruit Juice Industry*, Journal of Chromatography A, (1997), vol. 770, pp. 243-252.

Tyre, et al., *Treatment of Four Biorefractory Contaminants in Soils Using Catalyzed Hydrogen Peroxide*, J. Environ. Qual., (1991), vol. 20, pp. 832-838.

Vogel, et al., *Transformations of Halogenated Aliphatic Compounds*, Environ. Sci. Technol., (1987), vol. 21, No. 8, pp. 722-736.

\* cited by examiner

US 8,048,317 B2

GENERATION OF FREE RADICALS, ANALYTICAL METHODS, BACTERIAL DISINFECTIONS, AND OXIDATIVE DESTRUCTION OF ORGANIC CHEMICALS USING ZERO VALENT IRON AND OTHER METALS

CROSS-REFERENCE TO RELATED APPLICATIONS

This application claims priority under 35 U.S.C. §119(e) of U.S. Provisional Application No. 60/636,018, filed Dec. 13, 2004, which is entirely herein incorporated by reference.

BACKGROUND OF THE INVENTION

1. Field of the Invention

This invention relates to use of zero valent iron and other metals to generate hydroxyl free radicals and undergo subsequent oxidation to destroy organic chemicals and disinfect bacteria, and in the quantitative analysis of 2-thiobarbituric acid-reactive substances such as ascorbic acid and carbohydrates.

2. Description of the Related Art

Destruction of halogenated hydrocarbons (RX) by means of using zero-valent metals such as iron ($Fe^0$) (Sweeney and Fisher 1972; Sweeney 1981; Senzaki and Kumagai 1988, 1989, 1991; Gillham 1993; Matheson and Tratnyek 1994; Rima et al. 1999, 2001) is one of the technologies currently studied for either in situ or aboveground treatment of groundwater. $Fe^0$ is a mild reductant that can reductively dehalogenate RX according to the equations 1a-c. The reaction in the equation 1a is thermodynamically favorable (Vogel et al. 1987). Since the oxidation of $Fe^0$ to $Fe^{2+}$, equation 1b, is thermodynamically favorable (Weast 1984), the reduction of RX by $Fe^0$, equation 1c, should be favorable.

(1a)

(1b)

(1c)

Cheng et al. (2002) have studied the destruction of organic pollutants by mild process, and examined methods of aqueous activation of oxygen gas ($O_2$) at room temperature for this purpose. The scheme is based on zero-valent iron, air, and iron ion chelators. Generation of hydroxyl radicals was proposed, but not confirmed or proved. Cheng et al. (2002) hypothesized that the following three reactions are important to the overall scheme.

(2)

(3)

(4)

where L is an organic compound.

Using the equations 2-4, Cheng (2002) intended to explain the complete mineralization of chlorinated phenol, polychlorinated biphenyls (PCB's), nitroaromatics, and organophosphorous compounds. The detected products of this reaction are carbon dioxide ($CO_2$), oxalate, succinate, and propionate.

SUMMARY OF THE INVENTION

One embodiment provides a method for the disinfection of water polluted by microorganisms comprising administering zero-valent iron to the water in the presence of oxygen.

Another embodiment provides a method of determining content of a thiobarbituric acid-reactive substance in a solution comprising administering zero-valent iron in the presence of oxygen and 2-thiobarbituric acid to the solution and measuring a concentration of a 2-thiobarbituric acid-complex.

DETAILED DESCRIPTION OF THE PREFERRED EMBODIMENT

Figure 1:
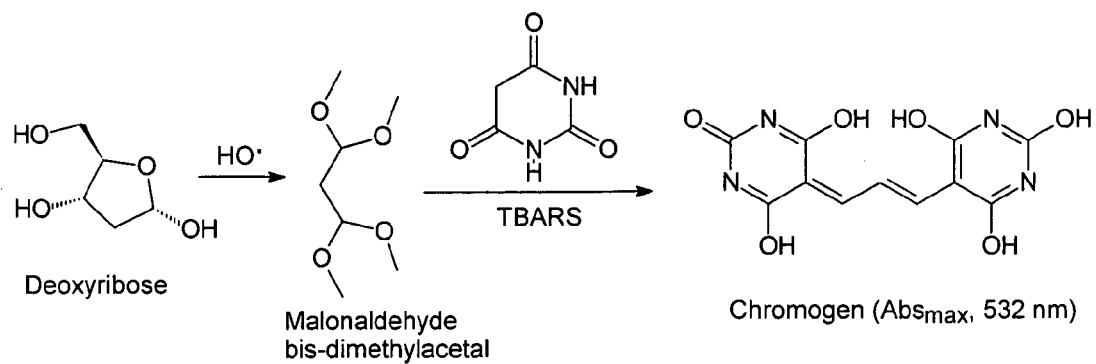
FIG. 1. Proposed mechanism of chromogen formation from reaction of deoxyribose and hydroxyl free radicals generated from zero-valent iron followed by reaction with thiobarbituric acid (TBA).

Many wastewaters originating in the chemical process industries contain high concentrations of organic chemicals that should be treated prior to discharge. Those chemicals often cause environmental pollution. Usually, those materials such as chloromethanes and DDT are difficult to destroy (Matheson and Tratnyek 1994; Hall et al. 1996; Gu et al. 1997 Ghauch et al 2001). For years, engineers have relied on various processes to make industrial wastewater "acceptably clean" by oxidation techniques, through which the contaminants are converted into carbon dioxide and water, which are ideal for treatment of wastewater containing one or more such organic pollutants. Each method, however, has its own drawbacks. The wet air oxidation process requires high temperature and high-pressure conditions and is, therefore, very energy consuming for diluted effluents. The ozonation techniques also demand a great deal of energy during operation. Other methods which involve $TiO_2$ and metal oxides as photocatalysts are being developed to degrade phenolic compounds.

Preferred embodiments herein include the use of iron (or in combination with other metals) coupled with oxygen gas, which can produce hydroxyl free radicals to degrade chlorinated and non-chlorinated organic compounds in aqueous solutions. Free radical reactions can also cause damage to lipids, proteins, membranes and nucleic acid, interrupt many biological processes, and lead to a variety of diseases. Among the reactive oxygen species, hydroxyl radical is one of the most active and strongest oxidant agents, and can react with almost any substance at a diffusion rate.

A hypothesis involving hydroxyl radicals can explain a substantially complete destruction of non-chlorinated and chlorinated chemicals, which include the industrial chemicals, such as phenols, chloroform, trichloroethylene, tetrchloroethylene, the pesticides heptachlor, carbaryl, atraizine, simazine, propazine, benomyl, picloram, dicamba, parathion, warafin, and warfare chemicals such as TNT. The degradation efficiencies can be related to the treatment conditions, metal species and/or combinations, and metal particles/powders. In addition, free radicals can be generated to react with a wide range of organic chemicals, such as carbohydrates for rapid analysis of the carbohydrates.

There has been no study previously to report formation of hydroxyl free radicals (HO.) in a mixture of zero-valent iron, bimetals [e.g., $Fe^0$ with nickel (Ni), palladium (Pd) and/or zinc (Zn)] and water. The inventors have successfully detected the formation of HO. hydroxyl radicals generated by zero-valent iron powder or bimetals in a buffer at acidic conditions. In certain embodiments, the buffer is an acetate buffer solution, phosphate buffer solution, or acidic buffer. In certain embodiments, the buffer is preferably an inorganic buffer. The inventors have utilized a wide range of applications of the radicals generated by $Fe^0$ for bacterial disinfection, domestic wastewater treatment, industrial water treatment, groundwater treatment, contaminated site remediation, analytical chemistry, etc.

The inventors have shown hydroxyl free radicals formation by zero-valent iron powder or bimetals (e.g., Fe—Pd, Fe—Cu, Fe—Pt, Fe—Co, Fe—Ru, Fe—Ni, Fe—Pd, Fe—Zn) in aerated buffer at acidic conditions. The free radicals are active molecule species that can react with many chemicals. Economical and efficient generation of free radicals and creative uses of the free radicals are among the features which may be found in preferred embodiments. The hydroxyl free radical (HO.) was indirectly observed by its reaction with the deoxyribose to form malondialdehyde (MDA). In one instance, this aldehyde can react with thiobarbituric acid in 15% acetic acid at about 100° C. to produce a pink chromogen which can be measured at about 532 nm. The inventors have demonstrated the following novel industrial applications of the processes described herein which generate hydroxyl free radicals, including, but not limited to:

a. Wastewater treatment of pesticides effluents
   b. Domestic wastewater
   c. Wastewater of petroleum effluent industries
   d. Wastewater of paper industries e. Disinfection of water polluted by bacteria and/or chemical contaminants
f. Wastewater of food industries
g. Hospitals wastewater
h. Remediation of chemically-contaminated sites
i. Analytical methodologies for quality control of carbohydrates in fruits and juices
j. Analytical methodologies for quality control of formulated drugs.

DEFINITIONS

The following definitions are provided.

Free radicals are chemical species that possess an unpaired electron in the outer (valence) shell of the molecule. This species can also be considered a group of molecular fragments that is capable of independent existence. Because they are highly reactive, they can have low chemical specificity; i.e., they can react with most molecules in the vicinity. They can gain stability by capturing the needed electron. As such, they do not stay in their original state for very long and quickly react with their surroundings. Hence, free radicals attack the nearest stable molecule, "stealing" its electron. When the "attacked" molecule loses its electron, it becomes a free radical itself, thus beginning a chain reaction. Once the process is started, it can cascade, finally resulting in the destruction of chemical species and even in the disruption of a living cell, e.g., bacterial death.

How Oxygen Free Radicals are Generated and How the Free Radicals can be Measured:

Electrons within atoms and molecules occupy regions of space known as "orbitals". Each orbital can hold a maximum of two electrons. A single electron alone in an orbital is said to be "unpaired" and a radical can be defined as any species that contains one or more unpaired electrons. Such a definition embraces the atom of hydrogen having one unpaired electron. The diatomic oxygen molecule, $O_2$, has two unpaired electrons and thus qualifies as a radical. For chemical reasons (Fridovich et al. 1983; Henderson 1983), $O_2$ likes to receive its electrons one at a time, producing a series of partially reduced intermediates.

Superoxide ($O_2^-$) ion is the one-electron reduction product of oxygen. Dissolved in organic solvents, it is an extremely reactive species, e.g., it can displace chlorine from chlorinated hydrocarbons as carbon tetrachloride ($CCl_4$) (Sawyer, 1979). In aqueous solution, $O_2^-$ is poorly reactive, acting as a reducing agent (e.g., it will reduce cytochrome c or nitro-blue tetrazolium) and slowly undergoing the dismutation reaction, in which one molecule of superoxide reduces another one to form hydrogen peroxide ($H_2O_2$). The dismutation reaction occurs in stages. $O_2^-$ must first combine with a proton to yield the hydroperoxyl radical, $HO_2$. (Equation 5)

$$O_2^- + H^+ \rightarrow HO_2 \cdot \quad (5)$$

$$HO_2 + O_2^- + H^+ \rightarrow H_2O_2 + O_2 \quad (6)$$

$$\text{overall } O_2^- + O_2^- + 2H^+ \rightarrow H_2O_2 + O_2 \quad (7)$$

At acidic conditions, high concentrations of $H^+$ ions accelerate the rate of dismutation and then hydrogen peroxide is generated (Equation 6). Hydroxyl radical is produced whenever $H_2O_2$ comes into contact with ferrous ions ($Fe^{2+}$) which can be formed from zero-valent iron at acidic conditions for example. Since both $H_2O_2$ and metal complexes are present in a solution, it is logical to assume that hydroxyl radicals (.OH) can form according to Equation 8.

$$H_2O_2 + Fe^{2+} \rightarrow OH^- + \cdot OH + Fe^{3+} \quad (8)$$

Direct evidence for .OH production is difficult to obtain. Many indirect methods exist for demonstrating the existence of .OH in vitro (Halliwell 1981). However, in vivo any .OH formed is likely to react so close to its site of formation that the use of these methods is impractical, although some techniques (such as the ability of .OH to convert dimethylsulphoxide into methane (Sawyer 1979) or its ability to hydroxylate aromatic rings in characteristic ways (Sawyer 1981)) show promise for in vivo use. Bacterial disinfection is also an indirect proof for the generation of free radicals. The TBA (thiobarbituric acid) test is one of the most widely used tests for measuring lipid peroxidation. The simplicity of performing the test (the material under study is merely heated with acid and TBA and the formation of a pink color measured at 523 nm) conceals its essential complexity. The pink color is due to the formation of an adduct between TBA and malonaldehyde (MDA) under acidic conditions. Indeed, the TBA assay is often calibrated with MDA and the results of peroxidation assays are often expressed as "amounts of MDA formed."

Hydroxyl free radical: The hydroxyl free radical is an extremely reactive oxidizing radical that will react to most molecules at diffusion controlled rates which means that reactions will occur immediately with molecules. The hydroxyl free radical is important in radiobiological damage and is several orders of magnitude more reactive towards cellular constituents than superoxide radicals (and many orders more reactive than hydrogen peroxide).

Around 1933, Fritz Haber and Joseph Weiss first proposed that hydroxyl free radicals (.OH) were produced from a reaction of superoxide and hydrogen peroxide:

$$H_2O_2 + O_2^- \rightarrow O_2 + \cdot OH + OH^- \quad (9)$$

This formula is called the Haber-Weiss reaction.

Henry Fenton had observed that the reducing agent, ferrous iron ($Fe^{2+}$), together with hydrogen peroxide could oxidize some organic compounds. The mechanism is now known to involve hydroxyl radicals, with a key step analogous to the reaction (9) but with the electron donor, $O_2^-$ replaced by $Fe^{2+}$:

$$H_2O_2 + Fe^{2+} \rightarrow OH^- + \cdot OH + Fe^{3+} \quad (10)$$

Oxidative destruction: Oxidation destruction is a reaction between organic compounds and hydroxyl free radicals generated by iron as shown in the following reaction:

$$Fe^0 + O_2 + 2H^+ \rightarrow Fe^{2+} + H_2O_2 \rightarrow Fe^{3+} + \cdot OH + OH^- \quad (11)$$

This oxidation reaction can lead to the mineralization of organic compounds, cell death, or bacterial death.

Scavenger: A reagent used for scavenging or binding, especially of a reactive or transient species. Scavenging in radiation chemistry means binding of radicals, free electrons, or free radicals with a scavenger.

Chromogen: A molecule with a chromophore that is colorless until the chromophore is modified chemically.

PAHs: Polynuclear (or polycyclic) aromatic hydrocarbons (PAHs) are a class of organic aromatic compounds, some of which are persistent and carcinogenic. PAHs are generally formed from the combustion of organic material and are ubiquitous in the environment.

Ascorbic acid: It is also known as vitamin C. It is a water-soluble vitamin important for the construction of connective tissues. A lack of vitamin C can cause abnormalities of the spine and a reduction in the ability of the body to heal wounds. Other deficiency symptoms may be seen, depending on species. Vitamin C is a natural antioxidant and can function as a scavenger to trap free radicals and reactive oxygen species. It is used in beverages such as beers to reduce oxygen content and thus preserve the beverage. Vitamin C can be found in fruits such as citrus fruits, potatoes and green vegetables.

Streptococci: A genus of spherical Gram-positive bacteria occurring in chains or pairs. They are widely distributed in nature, being important pathogens but often found as normal commensals in the mouth, skin, and intestine of humans and other animals. They are also common contaminants of milk and milk products.

E. coli: E. coli enteritis is a type of bacterial gastroenteritis, caused by a pathogenic strain of *Escheria coli*. The symptoms are a result of toxins or bacterial invasion into the intestine. The incubation period is about 24 to 72 hours. In adults, the infection is usually not severe, but in children and infants, the infection frequently requires hospitalization, and in some cases is life threatening.

Taking into account these definitions, one preferred embodiment is directed to oxidative destruction of chemical pollutants and bacterial disinfections by using zero valent iron and its combination with other metals under well-defined conditions.

In the methods which follow, the zero-valent iron (ZVI) and bimetallic compounds are preferably in the form of a powder. Powders having an average particle size of about 40 mesh to 325 mesh are preferred for use with some methods. Preferred bimetallic compounds include bimetals of ZVI with another element such as cobalt, 40% copper 40%, nickel 40%, palladium 1%, platinum 1%, rubidium 2%, and zinc 40%. The ratio of ZVI to the other metal in bimetallic compounds preferably falls within the range of about 40:60 to about 99:1 (Fe:other metal, by weight). In the methods discussed herein, ZVI may be used alone, a bimetallic compound may be used alone, ZVI may be used in combination with one or more bimetallic compounds, or a combination of one or more bimetallic compounds may be used. Reference to use of one type in a description of an embodiment or an example should not be taken as limiting, and it should be understood that any of the aforementioned metal materials may be substituted.

The methods which follow are preferably conducted at an acidic pH (below pH 7), including pH 2 to about pH 6.8, pH 3 to about pH 6, and about pH 4 to about pH 5.5. Buffer solutions may be used to maintain pH in a desired range. The reactions are also preferably done in the presence of oxygen. The oxygen may be what is naturally present in the solution (i.e. no additional steps are taken to add additional oxygen), or oxygen may be added to the solution, such as by bubbling oxygen gas or air through the solution, before and/or during the reaction, constantly or intermittently. In one preferred embodiment, oxygen or air is bubbled through the solution at a rate of about 0.5 to 15 Liters/min. The methods may be performed at ambient temperature or at temperatures between about 20° C. to about 35° C., unless specified otherwise.

Analytical Methods

In one aspect, certain preferred embodiments are directed to chemical analysis via chemical derivatization by the hydroxyl free radicals produced by zero valent iron powder (ZVIP) or its combinations with other metals. Although the embodiments, examples and description may reference ZVIP or a particular bimetal or metal combination, it is understood that the methods are not to be so limited. These embodiments exemplify new analytical methodologies for analysis, including quantitative analysis, of carbohydrates in solutions, such as juices and soft drinks, and vitamin C in samples, such as food supplements.

Preferred embodiments demonstrate scavenging of the hydroxyl free radicals derived from ZVIP by sugars or other molecules, which can produce a specific byproduct characterized by its reaction with thiobarbituric acid. The inventors use such series of reactions to develop a new methodology for the rapid identification and quantification of thiobarbituric acid-reactive substance.

Identification of thiobarbituric acid-reactive substance can be performed in any type of solution. A thiobarbituric acid-reactive substance is a compound that can react with thiobarbituric acid directly or via an intermediate or byproduct that can be derived from a reaction between free radicals with organic compounds such as aldehydes, ketone, and polyphenols, carbohydrates, sugars, and ketone acid. A typical procedure is to mix ZVI and a sugar-like compound in aerated acidic solution. When the intermediate or byproduct is formed, it is reacted with thiobabutiric acid-in acidic solution at elevated temperature to form a color complex for quantitation. Preferred embodiments include particular substances, such as carbohydrates (including, but not limited to sugars such as glucose, fructose and the like) and vitamin C.

The thiobarbituric acid-reactive substance reacts to form a 2-thiobarbituric acid-complex. The 2-thiobarbituric acid-complex can be detected by spectroscopic techniques. A preferred spectroscopic technique includes visible absorption spectroscopy. Usually, a 2-thiobarbituric acid-complex is a pinkish to reddish color compound. Reaction time for formation of 2-thiobarbituric acid-complex can be short, such as under about 20, 10, 15, 10, 9, 8, 7, 6, 5, 4, 3, or 2 minutes. The intensity of the absorption of directly proportional to the amount of complex formed.

In a preferred embodiment, a solution containing a 2-thiobarbituric acid-reactive substance can be assayed with zero-valent iron and 2-thiobarbituric acid. Preferably, the solution is an aqueous solution at a pH of less than about 6. More preferably, the solution is at a pH of less than about 5. In an embodiment, the solution is an acetate buffer (0.1M) at pH of about 4.6. The reaction preferably takes place in the presence of oxygen, dissolved in solution and/or $O_2$ or air added to the solution by blanketing, bubbling, or other suitable method.

In an embodiment, a sample of 2-thiobarbituric acid-reactive substance can be detectable in a solution at a range of concentration from of about 0.005 mM to about 50 mM. Preferably, a sample of 2-thiobarbituric acid-reactive substance can be detectable in a solution in a concentration range of about 0.05 mM to about 2 mM.

In an embodiment, zero-valent iron and/or one or more bimetallic compounds comprising ZVI can be incorporated into or added to a solution to achieve a concentration in the final solution of about 0.1 g/L to about 10 g/L. Preferably, the total concentration of zero-valent iron and/or bimetallic compounds is about 1 g/L to about 8 g/L. The zero-valent iron may be in the form of a powder and may be fully or partially dissolved or suspended in the solution. Bimetals, as described herein, and/or combinations of bimetals and/or zero-valent iron may also be used.

In an embodiment, a solution includes sufficient 2-thiobarbituric acid to achieve a concentration of about 0.1% (w/v) to about 5% (w/v). Preferably, the concentration of 2-thiobarbituric acid is about 0.5% (w/v) to about 1% (w/v).

Preferably, oxygen gas or air is in the solution, such as by bubbling through the sample, and/or by using a solution containing amount of dissolved gas.

Disinfection

In another aspect, the preferred embodiments are directed to disinfection of bacteria by the hydroxyl free radicals produced by zero-valent iron or bimetals of iron with other metals including, but not limited to, zinc, nickel, and palladium. Preferred embodiments contemplate the use of such metals, and combinations thereof, as reagents in the development and application of disinfection technologies for contaminated media such as medical wastes, water disinfections, and sterilization temperature-sensitive media.

Preferred embodiments demonstrate reaction of free radicals generated by zero-valent iron for use in disinfection of microorganisms in various matrices. Various matrices include any type of water in need of disinfection. Various matrices include, but not limited to, river water, wastewater, groundwater, swimming pools, domestic wastewater, industrial effluents, contaminated soil treatment, hospital liquid waste, petroleum liquid waste, industrial olive oil effluent waste, and the like.

Various microorganisms can be targeted for disinfection. In a preferred embodiment, a microorganism is a bacterium, preferably a pathogenic bacterium. Such microorganisms include, but are not limited to, coliform bacteria, E. coli, D. Streptococci, salmonella, pseudomonas, colera, parasites, fungi, and the like.

In an embodiment, zero-valent iron and/or one or more bimetallic compounds comprising ZVI can be incorporated into or added to a solution to achieve a concentration in the final solution of about 0.1 g/L to about 10 g/L. Preferably, the total concentration of zero-valent iron and/or bimetallic compounds is about 1 g/L to about 8 g/L. The zero-valent iron may be in the form of a powder and may be fully or partially dissolved or suspended in the solution. Bimetals, as described herein, and/or combinations of bimetals and/or zero-valent iron may also be used.

Preferably, oxygen gas or air is in the solution to be disinfected, such as by bubbling through the sample, and/or by using a solution containing amount of dissolved gas.

Reaction time for disinfection of the sample can be short, such as under about 100, 50, 40, 30, 20, 10, 15, 10, 9, 8, 7, 6, 5, 4, 3, or 2 minutes.

Oxidative Destruction

In another aspect, the preferred embodiments are directed to the oxidative destruction of chemical pollutants by the hydroxyl free radicals produced by zero-valent iron and/or its combinations with other metals.

Preferred embodiments demonstrate reaction of free radicals generated by zero-valent iron for use in disinfection of oxidative destruction of chemical pollutants. Various matrices include any type of water in need of oxidative destruction of chemical pollutants. Various matrices include, but not limited to, river water, wastewater, groundwater, swimming pools, domestic wastewater, industrial effluents, and contaminated soil, hospital liquid waste, petroleum liquid waste, industrial olive oil effluent waste, and the like.

In an embodiment, zero-valent iron and/or one or more bimetallic compounds comprising ZVI can be incorporated into or added to a solution to achieve a concentration in the final solution of about 0.01 g/L to about 10 g/L. Preferably, the total concentration of zero-valent iron and/or bimetallic compounds is about 1 g/L to about 8 g/L. The zero-valent iron may be in the form of a powder and may be fully or partially dissolved or suspended in the solution. Bimetals, as described herein, and/or combinations of bimetals and/or zero-valent iron may also be used.

Preferably, oxygen gas or air is in the solution to be disinfected, such as by bubbling through the sample, and/or by using a solution containing amount of dissolved gas.

Reaction time for disinfection of the sample can be short, such as under about 100, 50, 40, 30, 20, 10, 15, 10, 9, 8, 7, 6, 5, 4, 3, or 2 minutes.

EXAMPLES

The following examples are presented by way of illustration, not of limitation.

Example 1

Generation of Free Hydroxyl Radicals by Zero-Valent Iron Powder in Aerated Acetate Buffer Solutions at Low pH Free radicals are important intermediates in natural biological processes involved in cytotoxicity, control of vascular tone, and neurotransmission. The chemical kinetics of free-radical reactions control the importance of competing reaction pathways. Radiolysis is a powerful method to generate specific free radicals and measure their reactivity. Oxidation and reduction are chemical terms which describe the loss or gain of electrons by molecules, respectively. Thus, ferous iron ($Fe^{2+}$) is oxidized to ferric iron ($Fe^{3+}$) by the loss of a single electron, the charge on the ion changing from +2 to +3 in the process. Hydroxide ions in water ($OH^-$) can be ionized, losing an electron, to give hydroxyl free radicals (.OH); the unpaired electron in .OH is denoted by the radical 'dot', and such species have a strong tendency to restore the electron pair by pulling a hydrogen atom, complete with a single unpaired electron, from C—H bonds in sugars, in DNA, for example.

The hydroxyl free radical is important in radiobiological damage and is several orders of magnitude more reactive towards cellular constituents than superoxide radicals. The increasing interest in the role of free radicals in the pathogenesis of diseases has led to an increasing demand for techniques to measure free radicals and their reactions in vivo and, most importantly, in the clinical situations. Several problems arise when considering measurement of free radicals (Cheesman and Slater 1993). The first problem is the ultra-short half-life of free radicals (usually measured in microseconds). The second is that any free radicals produced in vivo react at or close to their source of formation. Hence, the methods devised to quantitate free radicals are more or less indirect (Slater 1984; Pryor and Godber 1991). A common analytical technique that measures free radicals is electron spin resonance spectrometry. However, it is relatively insensitive.

The inventors are interested in producing hydroxyl free radicals by zero-valent iron and other metals, and then exploring uses of the free radicals. It was decided to use an indirect method for the measurement of hydroxyl free radicals. This method is based on the scavenging of hydroxyl free radicals by deoxyribose. Various conditions were examined for efficient generation of the free radicals. The free radicals generated were evidenced by color formation and measured by a spectrophotometer.

1.1 Materials and Methods 1.1.1 Reagents

All reagents were of analytical grade. 2-Deoxy-D-ribose (D), 2,4,6-trichlorophenol (TCP), glacial acetic acid and sodium acetate trihydrate were purchased from Sigma Chemical Co. (St. Louis, Mo., USA). 2-Thiobarbituric acid (TBA) was obtained from Fluka AG (Buchs, Switzerland), and zero-valent iron powder (ZVIP) (325 mesh) was obtained from Merck (Darmstadt, Germany). Double-distilled water was deionized with Milli-Q water purification system (Millipore) and filtered by a Millipak 40 cartridge (0.22 u.m) before use.

1.1.2 Instruments

A Shimadzu UV-VIS 1650 PC spectrophotometer was used to record the absorption spectra. The pH values were measured with a WTW pH/mV Hand-Held meter 330/SET. The pH meter was calibrated with standard buffer solutions. A Varian 3800 GC/Saturn 2000 ion trap mass spectrometer (MS) was used. The GC column was ZB-1, 60 m, 0.25 mm i.d., and 0.25 μm film thickness. The oven temperature was programmed from 60° C. (hold for 2 min) to 280° C. at a rate of 4° C./min and then hold for 5 min at 280° C. The injector temperature was 250° C. The injection mode was splitless. The injection volume was 1 μL. The carrier gas was hydrogen at a flow rate of 1 mL/min. MS was operated in EI and full scan mode. Solvent delay was 8.5 min. Mass range was 40-250 amu. The trap and transfer line temperatures were 250 and 280° C., respectively.

1.1.3 Sample Preparations and Procedures

All experiments were carried out at room temperature (22±1° C.) in acetate buffer (0.05 M, pH 5.2). The ZVIP was treated with 200 mL of 1 M HCl for 10 min, and then washed with deionized water (400 mL) four times to remove all residual HCl and $Fe^{2+}$.

Deoxyribose and 2,4,6-trichlorophenol stock solutions were prepared at 2.4 mM and 200 mg/L, respectively. The final concentrations of deoxyribose (0.6 mM) and 2,4,6-trichlorophenol (0-150 mg/L) were prepared by performing appropriate dilution. The ZVIP was added to the vial containing 100 mL of deoxyribose solution or to the mixture of deoxyribose and 2,4,6-trichlorophenol solutions. The vial was sealed with a butyl rubber stopper, and shaken continuously for the duration of the experiment. For the analysis, 3 mL of sample solution was added to 3 mL of TBA in 15% acetic acid (1% of TBA, w/v). The mixture was heated in a water bath maintained at 100° C. for 15 min. Temperatures of 90 to 100° C., and times of about 10 min to about 15 min may also be used in alternate embodiments. After the mixture was cooled, the absorption spectrum of the mixture was measured.

For the correlation study between chromogen intensity and reaction time with ZVIP, ZVIP (final concentration of 5 g/L) was added to 0.6 mM deoxyribose in aqueous buffer solution at pH 5.2. With an interval of 1 min, an aliquot of 3 mL was taken from the bottle and mixed with an equal volume of TBA solution. After heating in the water bath, an absorption spectrum was recorded.

1.2 Results and Discussion

1.2.1 Detection of Hydroxyl Radicals and Absorption Spectrum of Chromogen

The reaction of deoxyribose and hydroxyl free radical has been discussed extensively in the literature (Aruoma 1993; Gutteridge 1984; Halliwell and Gutteridge 1981). The hydroxyl radicals attack deoxyribose to form products that react with TBA upon heating at low pH and yield a pink chromogen (FIG. 1).

Figure 2:
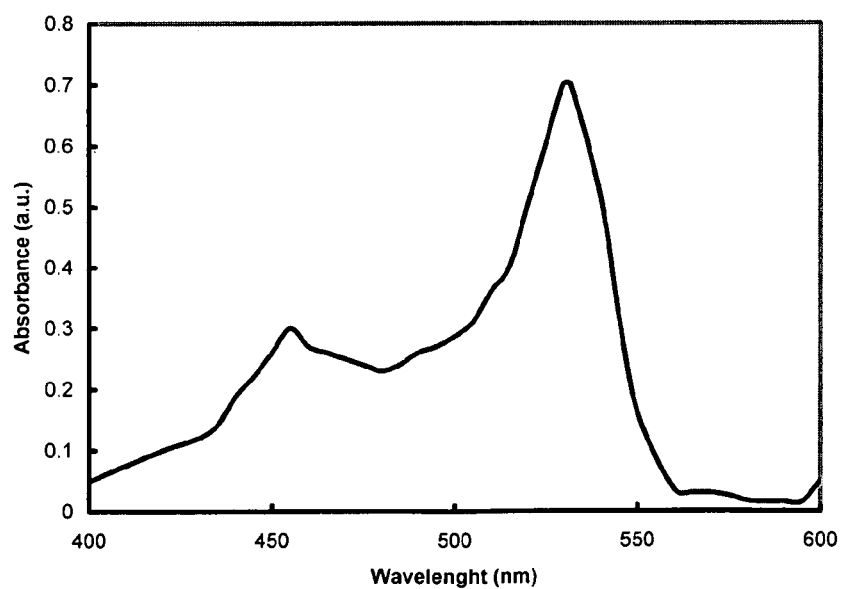
FIG. 2. Absorption spectrum of chromogen ($\lambda_{max}$ at 532 nm). An aliquot of 3 mL of TBA was added into an equal volume reaction mixture of iron and deoxyribose in acetate buffer solution, pH=5.2, and then was heated at 100° C. for 15 min.

FIG. 2 shows the absorption spectrum of the chromogen, which is identical to the spectra of malonaldehyde bis-dimethylacetal (MDA)-TBA adduct (i.e., chromogen) obtained by Kosugi (1987). There is one possibility to transform deoxyribose to MDA, which must be derived from a reaction between deoxyribose and hydroxyl free radicals. The hydroxyl free radicals are generated from ZVIP in aqueous buffer solution at an acidic condition (e.g., pH 5.2). This experiment supports our hypothesis proposed in the reactions (2-4).

1.2.2 Correlation Between the Amount of Iron and Chromogen Formation

Figure 3:
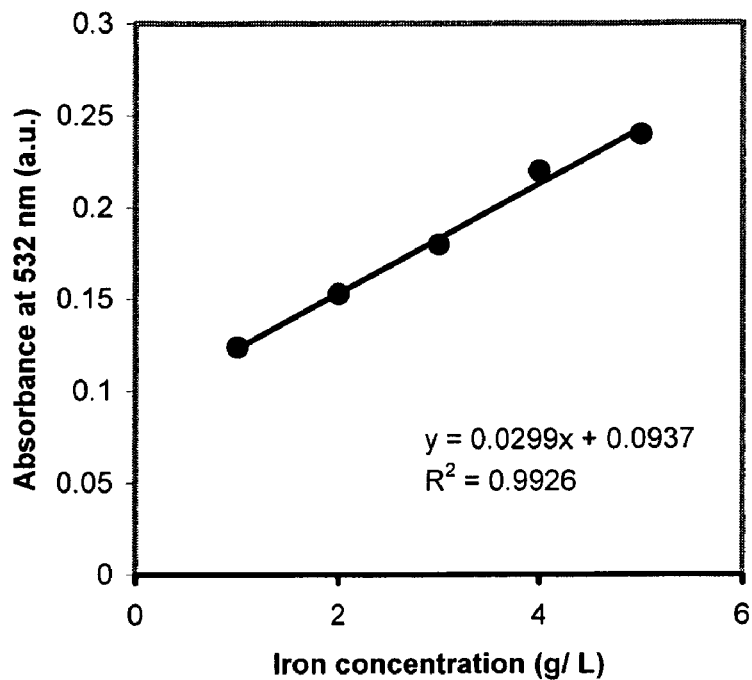
FIG. 3. Correlation between the absorbance of chromogen at the wavelength $\lambda$=532 nm and the amount of the iron powder. The amount of iron increased from 1 g/L to 5 g/L and the reaction time was 3 min.

The inventors have studied the correlation between the ZVIP amount and chromogen intensity. A linear correlation has been observed between the absorbance of chromogen and the amount of iron added in the aqueous buffer solutions (FIG. 3). The masses of the added iron increased from 1 g/L to 5 g/L and the reaction time for all the experiments was 3 min. The results show a clear correlation between the mass of iron and the intensity of chromogen.

Figure 4:
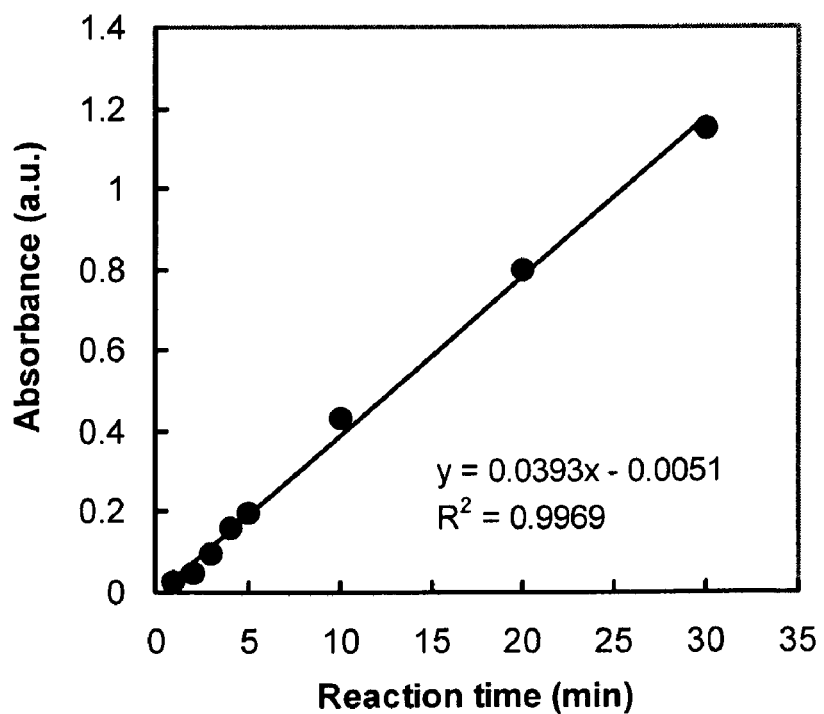
FIG. 4. Correlation between of absorbance at 532 nm and reaction time.

1.2.3 Correlation Between Chromogen Intensity and Reaction Time with ZVIP in Aqueous Buffer Solution The inventors studied the influence of reaction time on the chromogen formation. FIG. 4 shows that increasing reaction time results in an increase of hydroxyl radical generated and the amount of MDA produced, consequently more chromogen. The experiment had three replicates and the average relative standard deviation was about 2%.

Figure 5:
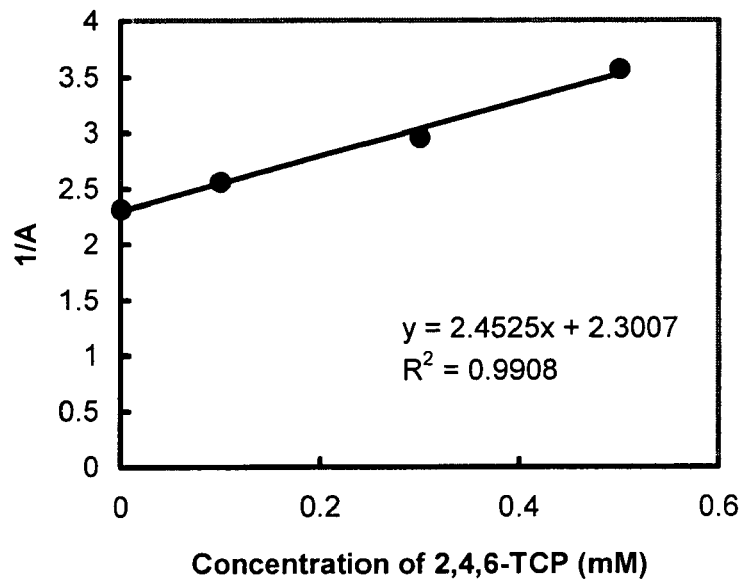
FIG. 5. Relationship between the reciprocal of maximum absorbance at 532 nm ($1/A_{532}$) and the concentration of 2,4, 6-trichlorophenol (TCP). TCP is a hydroxyl free radical (HO.) scavenger. The reaction constant ($k_S$) of TCP with HO. is calculated from the equation $k_S$=slope×$k_D$[D]$A_0$; where $k_D$ is $3.1 \times 10^9$ $M^{-1}$ $sec^{-1}$. $A^0$ is the absorbance in the absence of TCP or any other scavenger. [D] is the concentration of deoxyribose in the reaction mixture.

1.2.4 Competitive Reaction Between Deoxyribose and Scavengers with Hydroxyl Free Radicals In a reaction mixture, a competition reaction may exist between the scavenger (S) and deoxyribose to trap the free radical HO.. The trapping of HO. by scavengers decreases chromogen formation and thus decreases the intensity of its absorption spectra. The absorbance $A_o$ and A, respectively, without S and in the presence of S, are formulated in the following equation (Aruoma 1993).

$$1/A = 1/A_0 + \{k_S/k_D[D]A_0\}[S] \qquad (7)$$

Where $k_S$ and $k_D$ are the respective reaction constants between scavenger and deoxyribose molecules with hydroxyl radicals. A plot of $1/A=f(S)$ presented in FIG. 5 can be used to calculate the slope $k_S/k_D[D] A_0$ of the straight line in equation 7. The $k_D$ value available in the literature ($3.1 \times 10^9$ $M^{-1}$ $s^{-1}$) allows calculation of the $k_s$ value (the rate constant of reaction between S and HO.). The calculated $k_s$ value was $2.49 \times 10^{11}$ $M^{-1}$ $sec^{-1}$.

In summary, results in Example 1 show that zero-valent iron powder generates hydroxyl free radicals at appropriate conditions.

Example 2

Analysis of Fructose, Glucose and Sucrose in Fruit Juices by Using 2-thiobarbituric Acid and Zero-Valent Iron Powders The determination of individual sugar content in fresh fruits and vegetables and their juices is an important chemical analysis carried out to evaluate quality and to detect adulteration or contamination. Analytical techniques such as high performance liquid chromatography (HPLC) using different separation mechanisms (adsorption, size exclusion, or ion exchange) and various detectors (refractive index, UV absorption, amperometric, etc.), thin-layer chromatography (TLC), and gas chromatography (GC) have been commonly used for qualitative and quantitative analyses of fruit juices (Prodolliet and Hischenhuber 1998). While chromatographic techniques are very accurate, they are time-consuming and require tedious sample preparations. Sugar analyses carried out by enzymatic assays are specific, rapid and reproducible (Kunsst et al. 1984). However, the analyses require single determinations for each compound, which results in time-consuming procedures and high cost of analysis (Trifiro et al. 1997). Lanza and Li (1984) and Li et al. (1996) reported the application of Near Infrared (NIR) spectroscopy for the direct analysis of total sugar content in fruit juices. However, they concluded that it was not possible to determine individual sugars with acceptable accuracy or precision by using the transmission mode with a quartz cell path length of 2.2 mm. Giangiacomo and Dull (1986) developed NIR models based on transmittance measurements that predicted individual sugars (sucrose, glucose, and fructose) in aqueous mixtures with a standard error of prediction of 0.35-0.69. Improved sensitivity and accuracy for the quantitative analysis of individual sugars in juices have been accomplished by placing the liquid sample on a fiberglass support, eliminating the water and measuring the dry extract by diffuse reflectance spectroscopy (Alfaro et al. 1990; Li et al. 1996). Advances in Fourier transform NIR (FT-NIR) spectroscopic instrumentation and multivariate data analysis techniques have had significant impact in the determination of changes in food composition. FT-NIR improves spectra reproducibility and wave number precision (McClure et al. 1996) which can minimize the effects of solvent interference. However, the analysis of individual sugars by the techniques cited above are either very expensive or need extensive expertise or sophisticated instrumentation.

Preferred embodiment demonstrate scavenging of the hydroxyl free radicals derived from ZVIP by sugars, which can produce a specific byproduct characterized by its reaction with thiobarbutiric acid. The inventors use such series of reactions to develop a new methodology for the rapid identification and quantification of individual sugars in fruit juices.

2.1 Materials and Methods

2.1.1 Reagents and Instruments

All reagents were of analytical grade. Sucrose, glucose, fructose, lactose, glacial acetic acid and sodium acetate trihydrate were purchased from Sigma Chemical Co. (St. Louis, Mo., USA). The other reagents were the same as those used in Example 1. The instruments used were the same as those in Example 1

2.1.2 Standard Solution Preparation

All experiments were carried out according to the same procedures described in Example 1, except the pH value of the acetate buffer (0.1 M) was 4.6. The carbohydrate stock solutions were 15 mM. The working solutions of carbohydrates were made with appropriate dilution.

2.1.3 Sample Preparation

Fruit samples were pressed with a blender to obtain the juices. An appropriate dilution of the juices or the carbonated beverages was made with ionized water.

The juices or carbonated beverages were diluted in aqueous acetate buffer at pH 4.6. ZVIP (0.5 g) was added to 100 mL of the carbohydrate or juice solutions in a vial. After the vial was sealed with a butyl rubber stopper, it was shaken continuously for the duration of the experiment. The mixture was shaken at the same conditions as the standard solutions, and analyzed in the same manner as the standard solutions. Table 1 summarizes the experimental data of samples of sugars in mixtures and the preparation method of the internal standard addition procedure. The derivatization procedure was the same as that described in Example 1 except the buffer pH value was 4.6. The samples were diluted in the first step 150 times and prepared according to the protocol presented in Table 2.

2.2 Results and Discussion

Figure 6:
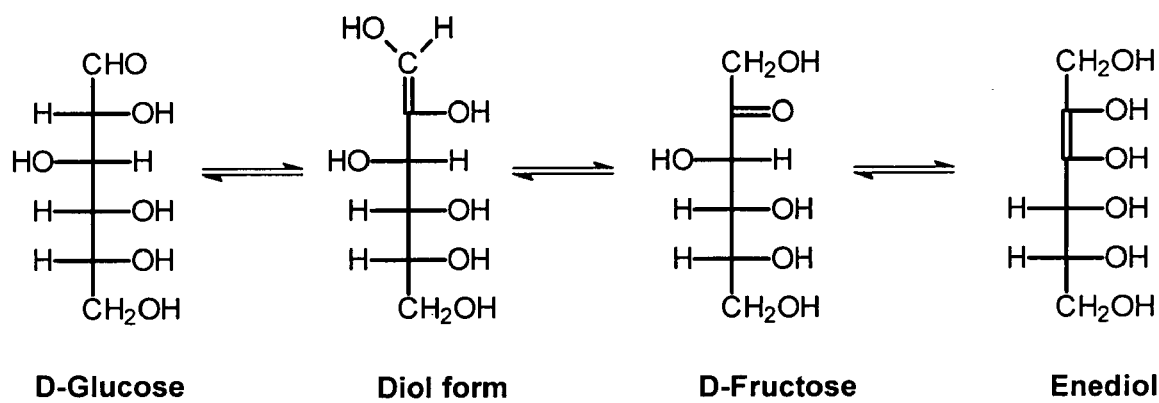
FIG. 6. Transformation between glucose, fructose, and their diol and enediol forms.
Figure 7:
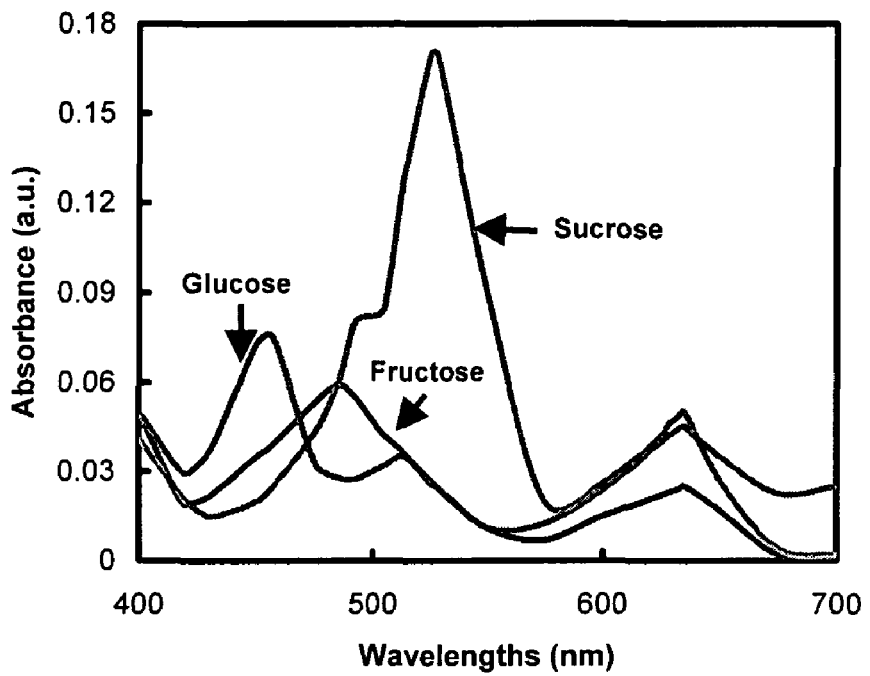
FIG. 7. Absorption spectra of fructose, glucose, and sucrose after reaction with iron and formation of a complex with TBA.

2.2.1 Reaction Nature and Specificity of Zero-Valent Iron with Carbohydrates According to the Lobry, de Bruy and van Ekenstein (1897) transformation, fructose and glucose can each form an enediol in either an acidic or basic solution (FIG. 6). Sucrose upon hydrolysis to glucose and fructose would be expected to give the same enediol structure. In aqueous solution at pH less than 7, ZVIP and the enediol can undergo hydrogenation and/or hydroxylation reaction similar to those observed by Sweeny (1981a&b, 1983). Sweeny showed both hydroxylation and saturation in the case of the iron-catalyzed reduction of chlorobenzene, where cyclohexanol is observed as a product. An aldehyde also can be formed during the oxidation of sugar (Hodge, 1967). The 2-thiobarbituric acid (TBA) test was discovered 50 years ago for the measurement of lipid oxidation. Since then, it has been widely used for the measurement of the oxidative state of biology and food materials. It had been proposed that the products obtained by oxidation present reactive substances with TBA and form characteristic complex. In the case of sucrose, glucose and fructose, the products of the reaction with hydroxyl free radicals derived from iron show visible absorption spectra specific for each of the sugars as shown in FIG. 7. The important analytical parameters are presented in Table 3.

TABLE 1

Experimental data of sugars in mixtures[a]

| | Concentration (mM) | | |
|---|---|---|---|
| Replicate | Fructose | Glucose | Sucrose |
| 1 | 1 | 1 | $Q_0^b$ |
| 2 | 1 | 1 | 0.5 |
| 3 | 1 | 1 | 1 |
| 4 | 1 | 1 | 1.5 |
| 5 | 1 | 1 | 2 |

[a]Concentration of sucrose to be found.
[b]No sugar control.

TABLE 2

Protocol of sample preparations for the measurement of fructose after 150-fold dilution. The time of treatment with iron is 10 min.

| Sample No. | Carbonated beverages | | |
|---|---|---|---|
| | Sprite ® | Caffeine free Pepsi ® | Mountain Dew ® |
| 1 | 2 mL sample + 6 mL acetate buffer + 0.1 g iron | 2 mL sample + 6 mL acetate buffer + 0.1 g iron | 2 mL sample + 6 mL acetate buffer + 0.1 g iron |
| 2 | 2 mL sample + 0.3 mL 15-mM fructose + 5.7 mL acetate buffer + 0.1 g iron | 2 mL sample + 0.3 mL 15-mM fructose + 5.7 mL acetate buffer + 0.1 g iron | 2 mL sample + 0.3 mL 15-mM fructose + 5.7 mL acetate buffer + 0.1 g iron |
| 3 | 2 mL sample + 0.5 mL 15-mM fructose + 5.5 mL acetate buffer + 0.1 g iron | 2 mL sample + 0.5 mL 15-mM fructose + 5.5 mL acetate buffer + 0.1 g iron | 2 mL sample + 0.5 mL 15-mM fructose + 5.5 mL acetate buffer + 0.1 g iron |
| 4 | 2 mL sample + 1 mL 15-mM fructose + 5 mL acetate buffer + 0.1 g iron | 2 mL sample + 1 mL 15-mM fructose + 5 mL of acetate buffer + 0.1 g iron | 2 mL sample + 1 mL 15-mM fructose + 5 mL acetate buffer + 0.1 g iron |

TABLE 3

Summary of the parameters of the method

| Carbohydrates | $\lambda_{Max}{}^a$ (nm) | LDR$^b$ (mM) | r$^{2c}$ | LOD$^d$ (mM) | RSD$^e$ % |
|---|---|---|---|---|---|
| Fructose | 490, 630 | 0.05–2.3 | 0.9912 | 0.01 | 4 |
| Glucose | 451, 520, 632 | 0.05–2.5 | 0.9992 | 0.01 | 4 |
| Sucrose | 490, 533, 632 | 0.02–2.5 | 0.9964 | 0.008 | 5 |

$^a$Maximum absorption.
$^b$Linear dynamic range.
$^c$Correlation coefficient.
$^d$Limit of detection.
$^e$Relative standard deviations.

2.2.2 Linearity and Detection Limit

Absorption linearity and LODs for the three sugars were determined. Fructose was determined from 0.05 to 2.3 mM (n=6) with a linear least-squares slope of 0.016, a y-axis intercept of −1.8, and a correlation coefficient 0.9912. Sucrose was determined from 0.05 to 2.3 mM (n=7) with a linear least-squares slope of 0.022 a y-axis intercept of −1.74, and a correlation coefficient of 0.9964, glucose was determined from 0.02 to 3.5 mm (n=8) with a linear least-squares slope of 0.0954, a y-axis intercept of −0.41, and a correlation coefficient of 0.9992. For the three linearity plots, at least points run in triplicate. The relative standard deviations (RSD) ranged from 4% to 5%. LODs were 0.01, 0.01, and 0.008 M for fructose, glucose and sucrose, respectively.

2.2.3 Quantitative Analysis of Sugars in Mixtures

Figure 8:
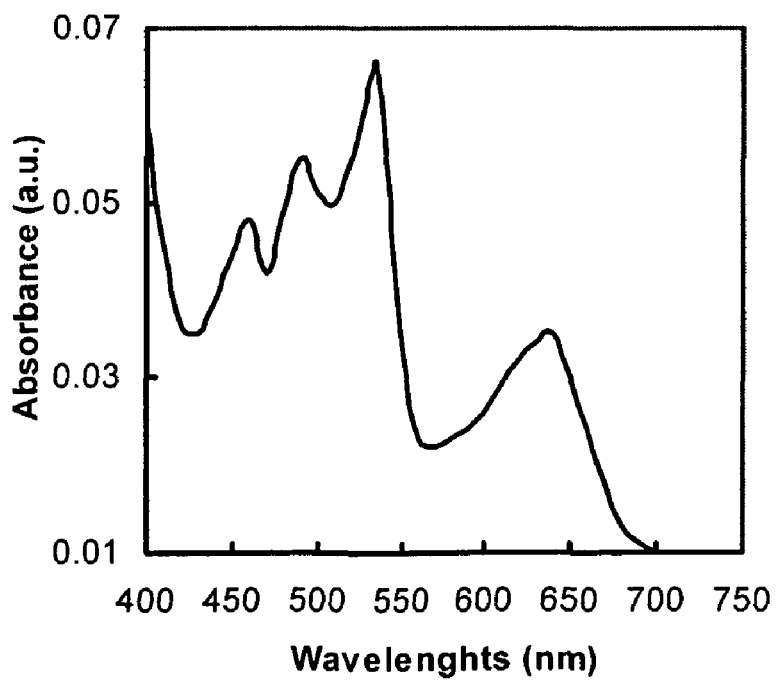
FIG. 8. Absorption spectrum of a mixture of fructose, glucose and sucrose (1:1:1 in weight) after reaction with iron and formation of a complex with TBA.
Figure 9:
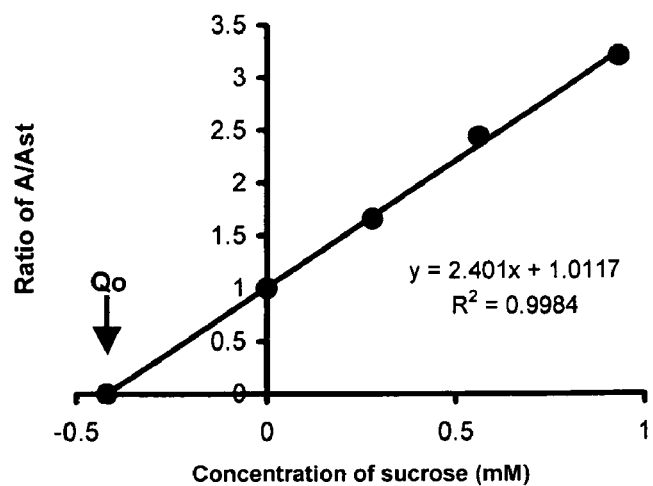
FIG. 9. Calibration curve of sucrose in a mixture of fructose, glucose and sucrose.

The samples that were fortified with sucrose, fructose and glucose were used to determine quantitative analysis when sucrose was considered the internal standard and glucose was the target analyte. The use of internal standard increases measurement accuracy. In the case of measurements other than glucose, we proceeded to change the internal standard and the unknown compound to be measured. FIG. 7 shows the absorption spectra of sucrose, fructose, and glucose. FIG. 8 presents the absorption spectra of a mixture of sucrose, glucose and fructose after treatment with iron and TBA. The extrapolation (FIG. 9) was performed from the regression curve $A^* = CQ^* + D$ representing the function $A^* = (A^*_o/Q_o) Q + A^*_o$ where $A^*$ is the normalized absorption intensity equal to the ratio of the solute absorption signal over the internal standard absorption signal. $Q_0$ is the solute concentration to be measured. $A^*_o$ is the normalized absorption intensity of the start solution. Q is the known concentration added and $Q_0$ is determined by the negative intercept of the curve with abscissa axis. Experimental data were found to be less than 10% errors (Table 4) as compared with the actual concentrations of sugars.

TABLE 4

Results for concentration determination of artificial mixture of three sugars

| Sugars | Concentration (mM) | | % Error |
|---|---|---|---|
| | Measured ($Q_0$) | Known (Q) | |
| Sucrose | 0.42 | 0.40 | 5 |
| Glucose | 0.63 | 0.59 | 7 |
| Fructose | 0.27 | 0.29 | 7 |

2.2.4 Determination of Fructose in Carbonated Beverages

The interest was to determine the concentrations of fructose in real samples such as carbonated beverages that contain high-fructose corn syrup. The composition of high-fructose corn syrup is about 55% fructose, 41% glucose, and 4% of other saccharides. The presence of ascorbic acid (vitamin C) and caffeine do not interfere with the measurements because their absorption spectra are completely separated. Fructose, glucose, and sucrose can be determined selectively using the characteristic absorption maximum of each sugar when complexed with TBA. After the analysis by the standard addition method, the average recoveries of measured values of fructose in comparison with the labeled value were 100% for Sprite (n=5), 99% for caffeine-free Pepsi (n=5), and 98% for Mountain Dew (n=5).

Carbohydrates such as fructose, glucose, and sucrose do not possess a good chromophore or fluorophore, which eliminates direct detection by standard UV/VIS spectrometry or fluorescence. Most carbohydrates do absorb light in near UV range (180-200 nm), but interference from other sample components and light transmission prohibit direct absorbance measurement. The reaction between iron and carbohydrates provides a possibility to perform determinations of three sugars individually or in a mixture. The results of this study demonstrate a concept of simple and quick method for the identification and analysis of fructose, glucose and sucrose. The preferred embodiments can be extended for the analysis of other oligosaccharides. It can also be conceptionalized a simple system based on this reaction with iron for monitoring of organic chemicals in water or soil.

This new method can offer quick, simple, economical and accurate determinations of the type and concentration of carbohydrates for a number of applications, but not limited to, as follows.

Standards of Identity—foods must have compositions which comply with government regulations;

Nutritional Labeling—to inform consumers of the nutritional content of foods;

Detection of Adulteration—each food type has a carbohydrate "fingerprint";

Food Quality—physicochemical properties of foods such as sweetness, appearance, stability and texture depend on the type and concentration of carbohydrates present;

Quality Control for Sugar-containing Products—Food manufacturers have to monitor their product quality for ingredient contents;

Food Processing—the efficiency of many food processing operations depends on the type and concentration of carbohydrates that are present.

In summary, this novel method is fast, simple, and economical for measurement of carbohydrates in food, juices, etc. It meets the needs of producers, consumers, regulators, official authorities, research laboratories and industries.

Example 3

Analysis of Ascorbic Acid (Vitamin C) in Fruit Juices and in Drug Formulations Ascorbic acid, also known as vitamin C, possesses intrinsic biological properties and functions. L-Ascorbic acid is involved in multiple important cellular functions in animals and plants. It functions as a cofactor in enzymatic process (Deutcsh et al. 1994), a powerful scavenger of free radicals (Deutcsh and Kolhouse 1993; Deutcsh et al. 1965), and most significantly as an antioxidant (Frei et al. 1989). Because ascorbic acid is such a good reducing agent, its function as an antioxidant has been reported to prevent collagen damage and inhibit oxidative and peroxidative damage of proteins and plasma lipids (Frei et al. 1989, Mukhodhyay and Chatterjee 1994a&b). Ascorbic acid has been the subjects of intense and on-going research. Pachla and co-workers (1985) had reviewed the methods for ascorbic acid analysis. A great variety of techniques including colorimetry (Sultan et al. 1994), GC (Deutcsh et al. 1994), HPLC (Kishida et al. 1992, Kissinger and Pachla 1987), electrochemistry (Kim H J 1989) 1989), microfluorometry (Martin et al. 1998) and spectrophotometry (Ferreira et al. 1997, Aray 1997, Lau et al. 1986, Thenelis 2001). Deutsch and Weeks (1965) developed what is now one of the standard methods for the determination of ascorbic acid using fluorometry. In their procedure, ascorbic acid is oxidized to dehydroascorbic acid which is then condensed with o-phenylenediamine to produce a quinoxaline, which is the chromophore for measurement.

This Example illustrates the use the free radicals generated by ZVI for the determination of ascorbic acid. This method is based on the oxidation reaction between ascorbic acid and zero-valent iron powder and followed by the 2-thiobarbituric acid test.

3.1 Materials and Methods

The reagents used in this study were the same as those used in Example 2. The samples were prepared in the same way as Example 2. Table 5 lists the samples containing ascorbic acid and sugars in a mixture and the samples containing sucrose alone as an internal standard. Samples were measured with the TBA test described in Example 1 and the 2,6-dichlorophenolindolphenol method (Horwitz 1990). The instruments used in this study were the same as those used in Example 2.

TABLE 5

Ascorbic acid samples containing sucrose

| Analytes | Concentration (mM) of five samples | | | | |
| --- | --- | --- | --- | --- | --- |
| | No. 1 | No. 2 | No. 3 | No. 4 | No. 5 |
| Sucrose[a] | 1 | 1 | 1 | 1 | 1 |
| Ascorbic acid[b] | Q* | 0.5 | 1 | 1.5 | 2 |

[a]These samples all contain 1 mM of sucrose in addition to various concentrations of ascorbic acid. No. 1 sample contain no ascorbic acid.
[b]Concentration of ascorbic acid to be measured.

Figure 10:
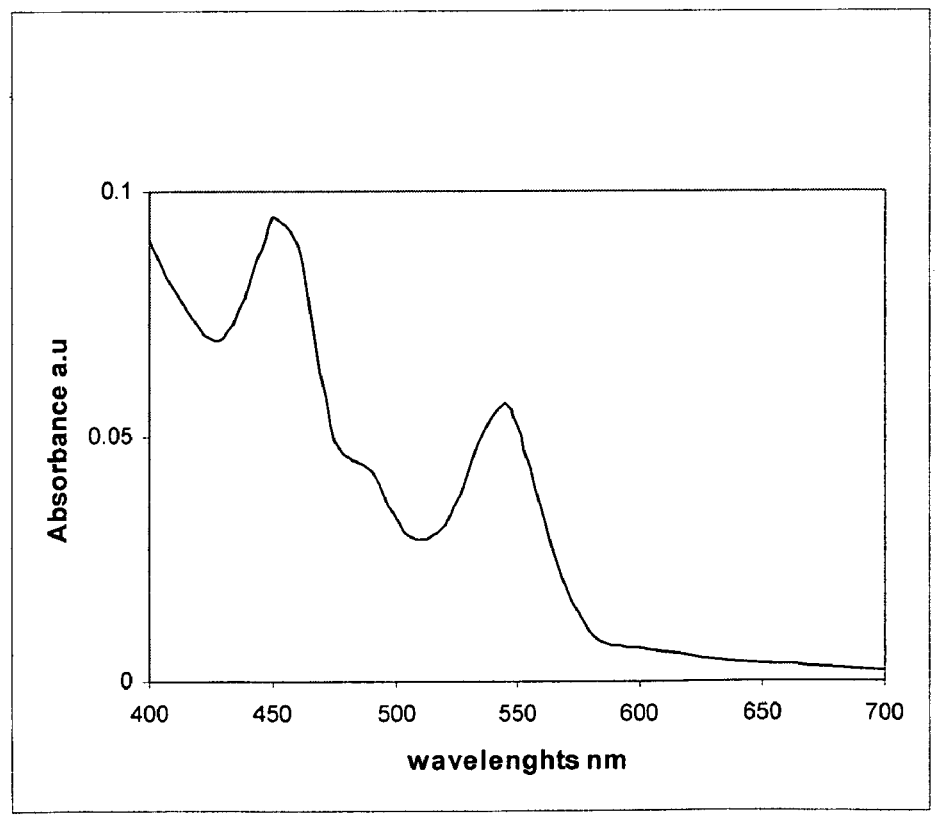
FIG. 10. Absorption spectrum of ascorbic acid after treatment with iron and TBA. Pure ascorbic acid (0.5 mg/mL in final solution) in acetate buffer (0.1 M, pH=4.6) was mixed with zero-valent iron powder at 5 g of iron/L. After the mixture was shaken for 3 min, an aliquot of 2 mL was transferred into 2 mL of TBA solution (1% TBA dissolved in 15% acetic acid) and heated for 15 min in water bath at 100° C.
Figure 11:
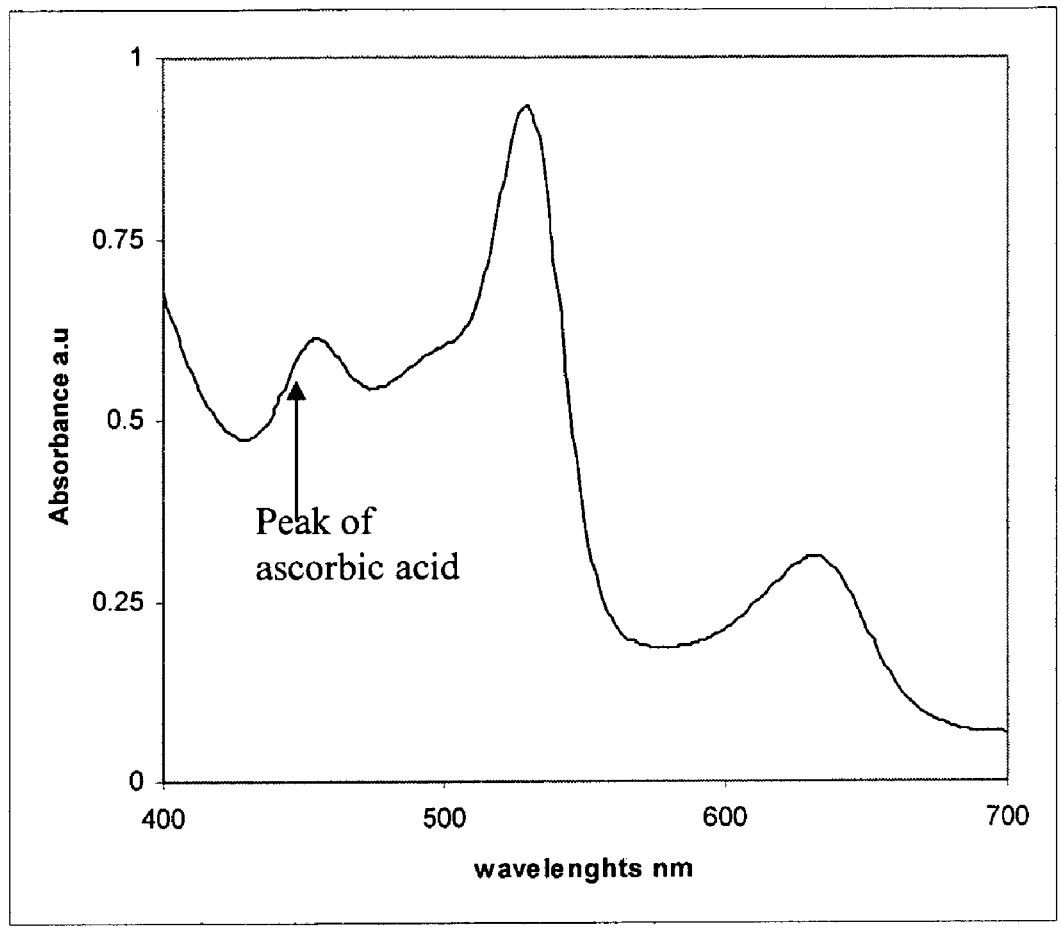
FIG. 11. Absorption spectrum of fruit juice after treatment with iron and TBA. Fruit juice was diluted 10 times with distilled water. The reaction condition is the same as that in FIG. 10.

3.2 Results and Discussion 3.2.1 Reaction Nature and Specificity of Zero Valent Iron with Ascorbic Acid In the case of ascorbic acid, the colored products obtained from its reaction with ZVI and TBA give a visible absorption spectrum specific for ascorbic acid as shown in FIG. 10, which shows two maximums at 450 nm and 535 nm. The analytical parameters are presented in Table 6. FIG. 11 shows an absorption spectrum of ascorbic acid in fruit juice after ascorbic acid was derivatized with TBA and ZVI. In this spectrum, the absorbance of ascorbic acid derivative doesn't interfere with that of glucose, fructose or sucrose that may be present in the samples, especially in fruit juices.

3.2.2 Quantitative Analysis of Sugars in Mixtures

Figure 12:
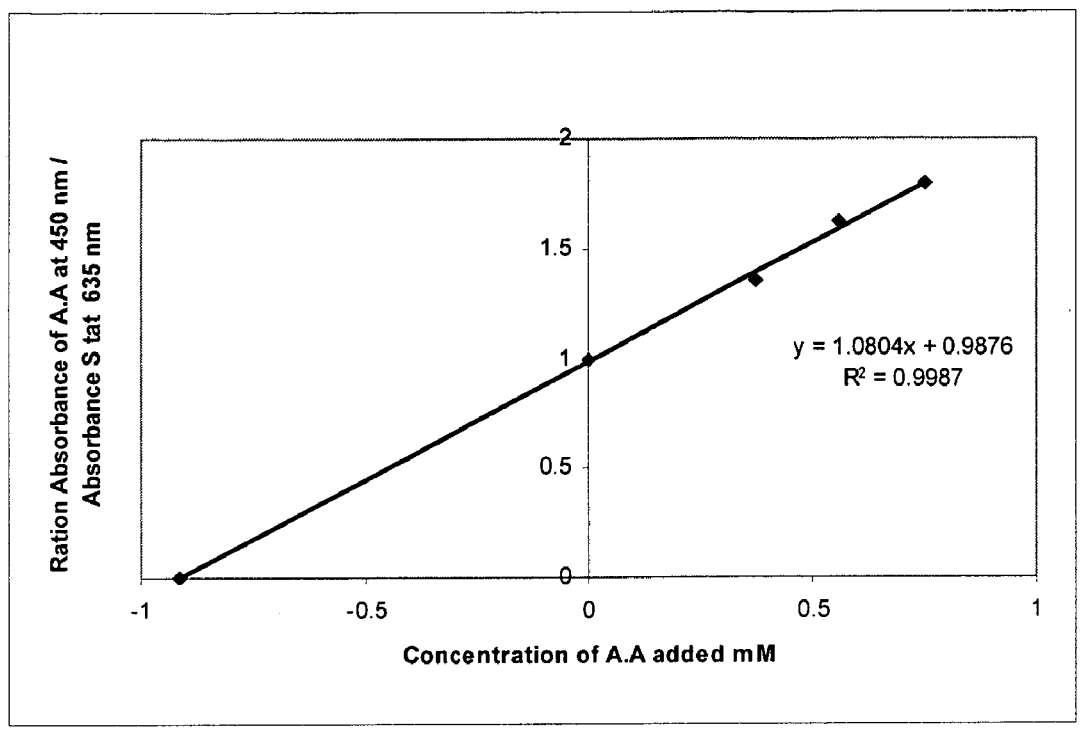
FIG. 12. Calibration curve for ascorbic acid in fruit juice where sucrose was used as an internal standard. Maximum absorbance of ascorbic acid derivative is at 450 nm ($\lambda_{450}$) and that of sucrose at 635 nm ($A_{635}$).

The samples that were fortified with ascorbic acid and sucrose were used to determine quantitative analysis when sucrose was considered the internal standard and ascorbic acid was the target analyte in the mixture (FIG. 12). The use of an internal standard increases accuracy in measurements.

TABLE 6

Analytical parameters of carbohydrates and ascorbic acid

| Parameters | Analytes | | | |
| --- | --- | --- | --- | --- |
| | Ascorbic acid | Fructose | Glucose | Sucrose |
| Absorption maximum (nm) | 450, 535 | 490, 630 | 451, 520, 632 | 490, 533, 632 |
| Linear dynamic range (mM) | 0.05–2 | | | |
| $r^2$ | 0.999 | | | |
| Limit of detection (mM) | 0.01 | | | |
| Relative Std Deviation % | 2 | | | |

(LOD is 0.01 mM. LDR is 0.05–2 mM.)

3.2.3 Application

In order to evaluate the application values of this new method for the analysis of ascorbic acid in real samples, the inventors employed it to measure ascorbic acid in fruit juices and pharmaceutical samples, and compared the results with those obtained by following the standard method (Horwitz 1990). The measured values were also compared with the values that the manufacturers certified. The measured concentrations of ascorbic acid in various food supplement tablets and fruit juices quantitatively agreed with the values that manufactures certified (within 10% errors) as well as those by the standard method (Table 7). For example, the ascorbic acid values measured by this new method were 100% of the labeled values in vitamin C Algorithm Lebanon (n=5), 98% in vitamin C Sun Market (n=5) and 97% in Tropicana® juice (n=5).

TABLE 7

Comparison of ascorbic acid concentrations determined by the new method, by the standard method and the labeled values in fruit juices and food supplements

| Matrices | Concentrations of ascorbic acid | | |
| --- | --- | --- | --- |
| | New method | Standard method[a] | Manufacture certified |
| Vitamin C Algorithm Lebanon | 998 mg/tablet | 985 mg/tablet | 1000 mg/tablet |
| Vitamin C Farmaline Lebanon | 63 mg/tablet | 58 mg/tablet | 60 mg/tablet |
| Vitamin C Sun Market | 490 mg/tablet | 497 mg/tablet | 500 mg/tablet |
| Lbbis Juice | 243 mg/L | 246 mg/L | 250 mg/L |
| *Bonjus* juice | 246 mg/L | 2434 mg/L | 250 mg/L |
| Tropicana Juice | 242 mg/L | 247 mg/L | 250 mg/L |

[a]Horwitz 1990

In summary, the data in Example 3 illustrate the use the free radicals generated by ZVI for rapid analysis of ascorbic acid in fruit juices and formulated food supplements. The preferred embodiments can be also used for the analysis of other food nutrients and supplements such as dyes, phenolic contents, carotenoids, vitamin E and other antioxidants.

Example 4

Mineralization of Phenol by Hydroxyl Free Radicals Generated from ZVI in Aqueous Buffer Solutions Phenol is often used by various industries and found in various consumer goods. Therefore, contamination of soil and groundwater by phenol is common in the world. Many remediation technology demonstration projects were conducted for cleaning up the sites contaminated by various organic pollutants including phenol. Some projects employed the technology of chemical oxidation.

It has been reported that Fenton process is very effective for the degradation of various organics in the presence of wastewater and soil (Barbeni et al. 1987, Bowers et al. 1989, Watts et al. 1990, Tyre et al. 1991, Dong 1993; Yang and Lai 1997, Yang 1999). Conventionally, $H_2O_2$ and $Fe^{2+}$ are used in the Fenton process for generating hydroxyl radicals to chemically destruct organic pollutants including phenol. Recently, a Fenton-like reaction using $ZVI/H_2O_2$ instead of $Fe^{e+}$ has been found to be effective in degradation of organic pollutants in wastewater and soil as well (Greenberg et al. 1997; Claudio Roberto et al 2005). In addition, ZVI has been successfully employed as a reductant in permeable reactive walls for the remediation of contaminated groundwater (Palmer et al. 1996; Gu et al. 1997; Warner et al. 1998). Electrokinetic remediation (EK process) is a technology that shows lots of promise. Therefore, some investigators combine the permeable reactive wall of iron powder, and Fenton-like reaction for the chemical destruction of organic contaminant(s) in the subsurface (Yang and Long 1998).

Use of ZVI has become an effective means to remediate environmental pollution exclusively on the basis of reduction reaction. It is inexpensive, easy to handle and effective in treating a wide range of chlorinated compounds or heavy metals. As abovementioned Examples demonstrate that ZVI generates hydroxyl free radicals, preferred embodiments include determination of the efficiency of ZVI at the conditions of hydroxyl free radical generation for the remediation of an aqueous solution of organic chemicals. Phenol is selected to be a model chemical to approve the concept and application values. The reaction of free radicals generated from iron with phenol leads to the complete degradation and to the formation of carbon dioxide and water. This process should be a valuable technology for the water treatment industries.

4.1 Materials and Methods 4.1.1 TOC Measurement

Total organic carbon (TOC) contents were measured with a Shimadzu TOC Analyzer model 5000 A. Blank controls (iron and water) were conducted without phenol. The TOC of phenol was measured before and after its reaction with ZVI. The TOC was calculated from the difference of total carbon (catalytic oxidation: 850° C., $O_2$, $CeO_2$) and total inorganic carbon (acidification by 10% $H_3PO_4$). A non-dispersive infrared detector was used to determine the formed carbon dioxide.

4.1.2 Measurement of Enthalpy Reaction and Carbon Dioxide Emission

A twin-type heat calorimeter (C80 Setaram) was used for calorimetric study and, hence, the heat generation behavior was analyzed.

An apparatus was designed and built to volumetrically measure the amount of carbon dioxide emitted. Briefly, carbon dioxide was emitted from the reaction between iron (3.5 g) and phenol (300 mL of buffer solution containing 50 ppm of phenol) under oxygen. The emitted carbon dioxide was collected into a sodium hydroxide solution (1 M). The volumetric titration method was performed to estimate the carbon dioxide collected.

All the other reagents and procedures are the same as Example 1.

4.2 Results and Discussion 4.2.1 Evolution of UV Spectra

Figure 13:
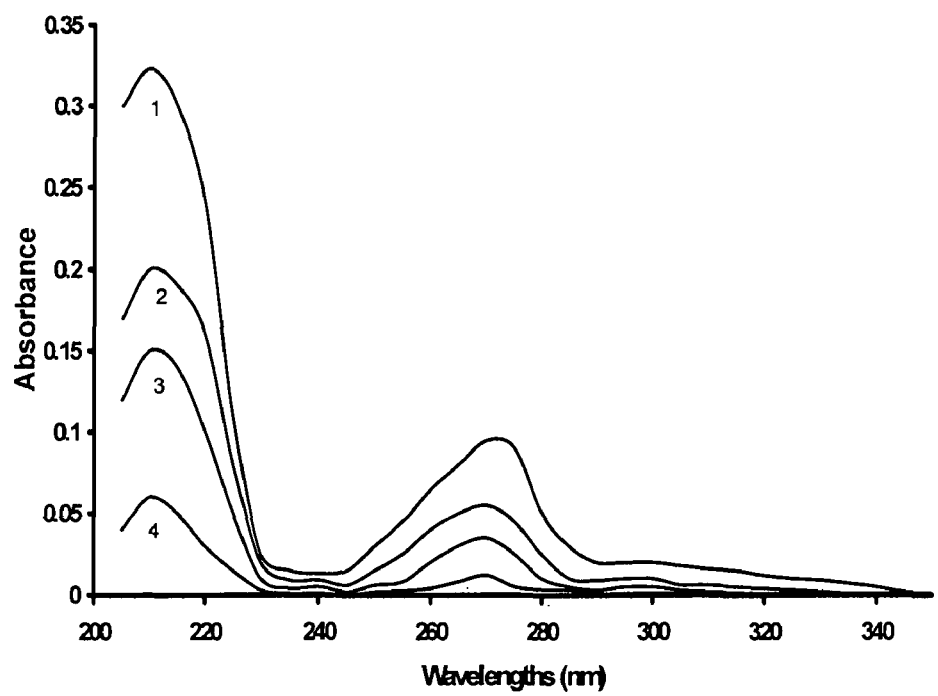
FIG. 13. Evolution of UV absorption spectra of phenol over reaction time after addition of iron powder in buffer solution, pH=4.8-5.5. The initial concentration of phenol was 10 μg/mL. 1=0 min, 2=2 min, 3=4 min, and 4=5 min.

The inventors proceeded to study degradation of phenol by hydroxyl free radicals derived from metallic iron, at first time, and the reaction was monitored with UV spectra for the disappearance of phenol. The UV absorption spectra of a phenol solution (10 mg/L) at our experimental conditions present maximums at 205 nm and 270 nm (FIG. 13, spectrum No. 1). After 3 min of the reaction (spectrum No. 4), we observed significant disappearance of phenol as monitored by UV absorption spectra. At 5 min, phenol became undetectable.

4.2.2 Influence of Oxygen and GC Chromatograms

Figure 14:
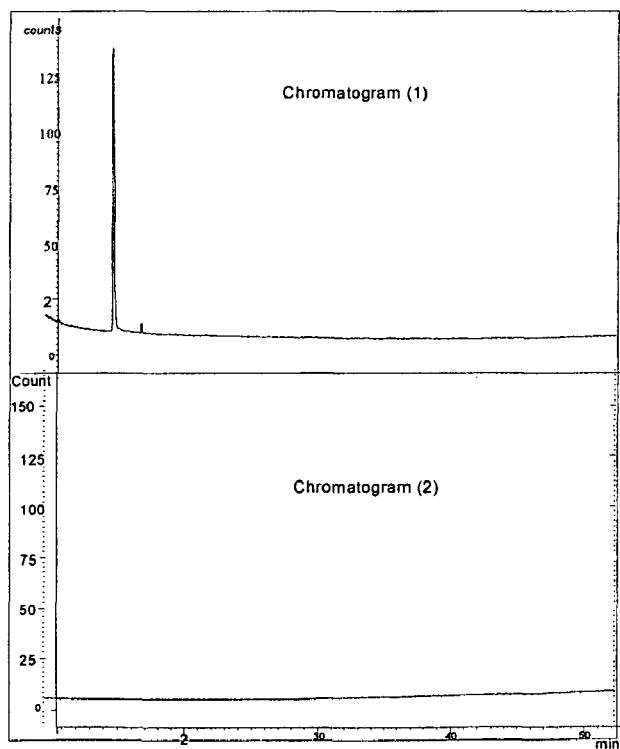
FIG. 14. GC chromatograms of phenol (1) before (100 ppm) and (2) after reaction with iron powder for 30 min while oxygen gas was bubbling. The reaction condition is the same as that in FIG. 13.
Figure 14B:
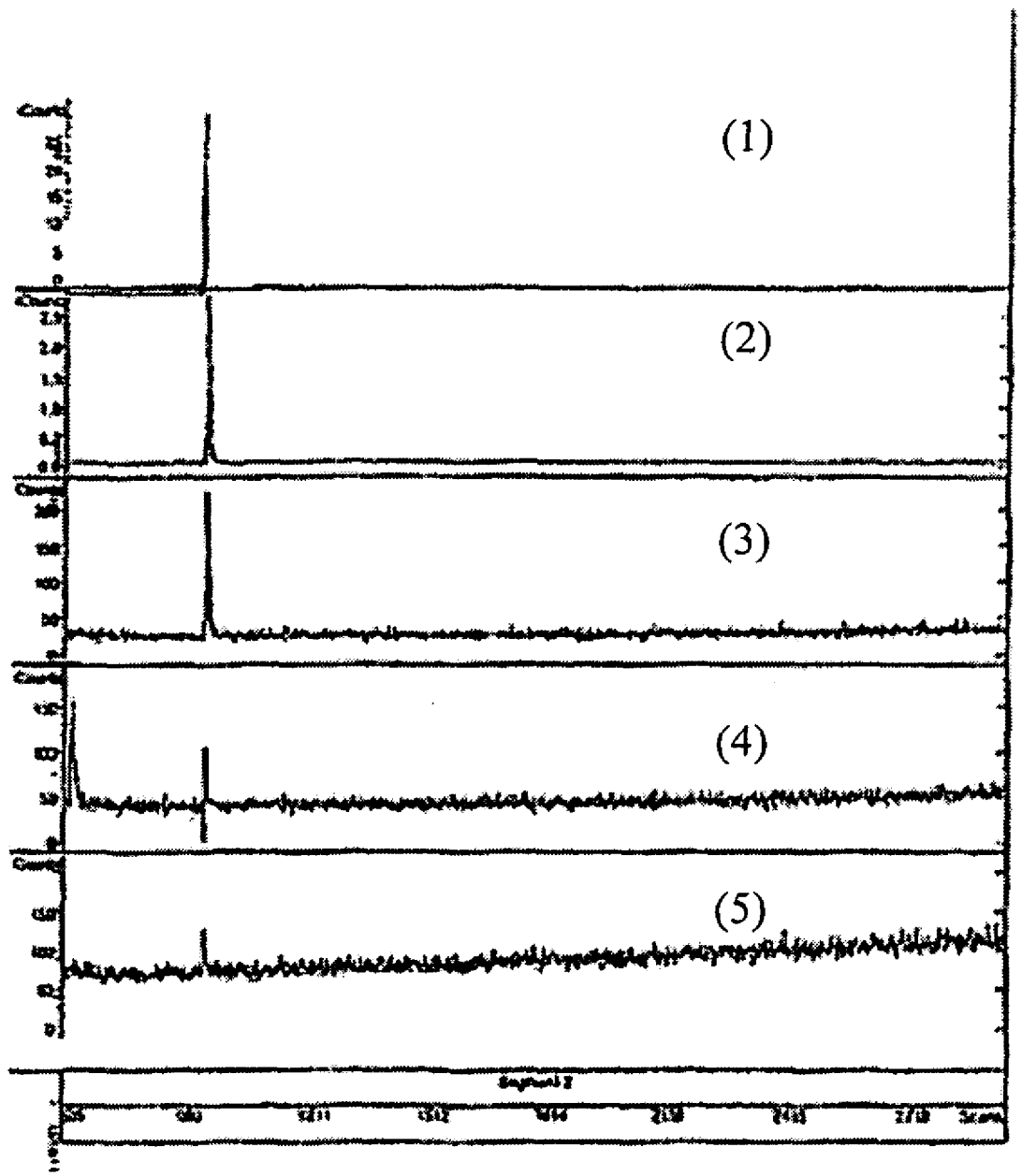
FIG. 14b. GC chromatograms of phenol before (100 ppm) and after reaction with iron powder for 30 min while nitrogen gas was bubbling. The reaction condition is the same as that in FIG. 13. After the treatment of phenol by iron, a peak was observed at the fragment 95 in (1), at the fragment 96 in (2), at the fragment 97 in (3), at the fragment 98 in (4), at the fragment 99 in (5).

Oxygen gas was bubbled through buffer solution containing iron powder and phenol. A complete disappearance of phenol has been observed, and no products were detected as shown in FIG. 14. It should be noted that if nitrogen gas was bubbled through the solution, hydrogenation of phenol was observed (FIG. 14b).

4.2.3 Complete Mineralization of Phenol

The total amount of phenol as TOC was measured before and after the reaction with zero valent iron powder (ZVIP). Table 8 shows phenol removal by different ZVIP quantities at different pH values. Phenol removal efficiency as TOC decrease was approximately quantitative (94-95%) when phenol (345 ppm) and iron (0.5 g/L) reacted for 10 min (Table 8). The removal efficiency increased as the quantity of iron increased. Reaction time and pH value of the reaction solution are also important parameters for phenol removal. The acidic pH needs to be maintained. The reaction is very fast, typically for 10 min.

TABLE 8

Removal of phenol measured as TOC decrease after ZVIP treatment

| | | | TOC (mg/L) | | |
|---|---|---|---|---|---|
| Phenol[a] (mg/L) | Iron (g/L) | pH | Prior reaction | After reaction[5] | TOC removal efficiency (%)[c] |
| Buffer blank | 5 | 4 | Buffered water | 29 | — |
| 345 | 1 | 4 | 957 | 230 | 79 |
| 345 | 5 | 4 | 957 | 78 | 95 |
| 345 | 5 | 6 | 917 | 88 | 94 |

[a] Phenol was dissolved in buffer (pH 4).
[b] The reaction underwent 10 min.
[c] The efficiency was corrected by subtracting the background value (29 mg/L TOC) from the TOC levels after reaction.

The inventors further verified the mineralization efficiency of phenol by ZVIP using enthalpy measurements. Calorimetric measurements were carried out with a Setaram Micro DSC C80 differential scanning calorimeter. The calorimeter enthalpies (AH) were calculated with the software built in the Seteram C80. Enthalpies were measured in both cases. The first case was zero-valent iron in buffer solution without phenol and the second was zero-valent iron and phenol mixed in buffer solution (pH 4). The average value of three replicates for the reaction enthalpy was $\Delta H°r = -162$ kJ·mol$^{-1}$. This value was very close to that obtained by calculation $\Delta H_{(calculated)} = -161$ kJ·mol$^{-1}$ (Organic Chemistry Data Booklet, 2001).

Carbon dioxide emission was also measured to confirm complete mineralization of phenol by ZVIP under acidic conditions. An amount of 36 mg of carbon dioxide was measured from a reaction of iron (3.5 g) in 300 mL of 50-ppm phenol in acidic buffer solution. The results again showed the mineralization of phenol by ZVIP.

In summary, the inventors proved the formation of hydroxyl free radicals from zero-valent iron at specific conditions, and have further employed the hydroxyl free radicals generated from metallic iron to destroy phenol, exemplifying non-chlorinated organic pollutants. The techniques described here can be directly or simply modified to degrade other organic chemicals such as polycyclic aromatic hydrocarbons (PAHs).

Example 5

Complete and Rapid Destruction of the Insecticide Heptachlor by Free Radicals Generated from Micro-Scale Iron and Iron-Nickel (Fe—Ni) Particles Over the past two decades there has been a strong movement to discontinue the use of numerous organochlorine pesticides, and the search for remediation methods addressing the existing pesticide accumulation has been pursued. Currently, there is no single method that can satisfactorily address the remediation of organochlorine pesticides. One approach that holds promise, however, is dechlorination. It is generally accepted that by removing the chlorine from organochloric compounds, the resulting hydrocarbon backbone is far less toxic. Reductive reaction by ZVIP can cause rapid and complete dechlorination of organochloric compounds. Furthermore, many methods involve complicated procedures such as anaerobic conditions, high-energy input, or several hours or even days to reach completion. Zero-valent iron alone has been demonstrated to dechlorinate DDT, however, palladized magnesium has been shown in some embodiments to be superior with regard to reaction time requiring 10 min compared to several hours or days for the former. Cheng (1997) proposed a detailed mechanism to explain the role of palladium in the hydrogenation process. It is based on the ability of palladium to intercalate hydrogen, which in turn acts as a powerful reducing agent at the palladium/zero-valent metal interface, where chlorinated organic compounds are likely adsorbed.

The preferred embodiments include generation of hydroxyl free radicals by bimetallic system. Experiments were conducted on destruction of the insecticide heptachlor by a Fe—Ni bimetallic system.

5.1 Materials and Methods

As noted hereinabove, the inventors propose that bimetallic metals will also generate free radicals as ZVIP does in Examples 1-4. The efficiencies of hydroxyl free radical generation will be increased with bimetallic metals such as iron (Fe) and nickel (Ni). Other combinations such as Fe/Pt, Fe/Pd, and Fe/Zn may also be used. Therefore, efforts were focused on testing the applicability of Ni—Fe (40% of Ni) (40%) bimetallic to treatment of contaminants. 12.3 g $FeSO_4.7H_2O$ and 3 g $NiCl_2.6H_2O$ were dissolved in 600 mL ultra pure with shaking at 120 rpm resulting in pH of solution in the range of 3.3 to 4.0. In one embodiment, the desired ratio of Fe to Ni is about 4:1. $NaBH_4$ solution was prepared by dissolving 6 g $NaBH_4$ in 400 mL ultra pure water. After adding the $NaBH_4$ black particles formed and then the mixture was shaken for another 20 min. The particles were then isolated by filtration.

Experiments were conducted to investigate the reaction of this bimetallic system with organic compounds. An amount of 0.5 g Fe—Ni was placed in contact with 100 mL of buffer solution containing heptachlor (340 µg/mL) in a glass vial. Oxygen gas was bubbling through the solution as the vial was shaken vigorously. Aliquots of samples were periodically taken with a syringe, and extracted with ethyl acetate (3×20 mL). The combined ethyl acetate extracts were dried over anhydrous sodium sulfate, and then concentrated to an appropriate volume for GC-MS analysis. The GC-MS and other instruments used in this study were the same as those described above.

5.2 Results and Discussion

Figure 15:
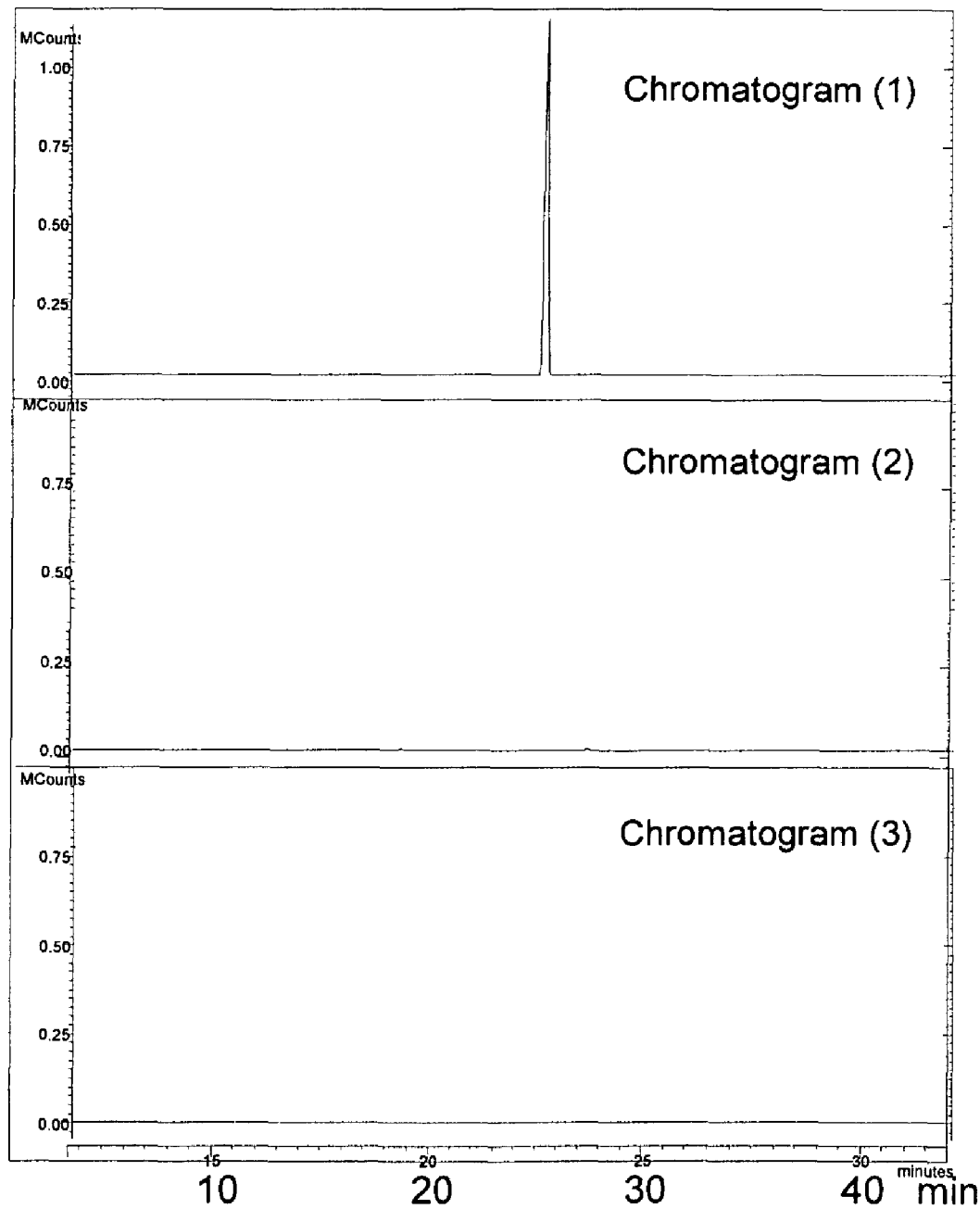
FIG. 15 GC-MS chromatogram of the insecticide heptachlor (1) before (340 ppm) (2) after 10 minutes of and (3) after 30 minutes of reaction with a mixture of microscale iron and nickel (4/6, w/w). The reaction condition is the same as that in FIG. 13.

As shown in FIG. 15, heptachlor was completely destroyed after 10 min of reaction. The complete disappearance of heptachlor strongly suggests that the free radicals are generated by the Fe—Ni system, which leads to the free radical reaction of heptachlor. The results show that Fe—Ni is more efficient than iron alone. Various bimetallic or multiple metallic systems should offer different efficiencies of free radical generation and subsequently a wide range of applications, and/or complete mineralization.

In summary, the preferred embodiments contemplate destruction of heptachlor and other organochlorine compounds by Fe and Fe—Ni bimetallic systems.

Example 6

Complete and Rapid Destruction of Phenol by Free Radicals from Micro-Scale Iron and Iron-Palladized (Fe—Pd) Particles Since the early 1990s, it has been known that elemental iron could be used to neutralize some chemicals. Investigators, searching for more efficient ways to remediate polluted water and soils, theorized that a bimetallic palladium/iron system might prove to be more effective than iron alone. Scientists in Arizona and Tennessee have developed a methodology using the two metals to remove volatile organic chemicals (VOCs) from water and soils, with only relatively harmless biphenyl and chloride ions as by-products. Complete mineralization was not observed Numerous experiments have pitted different batches of palladized iron containing varying ratios of the two metals against various contaminants. Through these experiments, the scientists dechlorinated the contaminants in a matter of minutes. Recently, researchers have succeeded in dechlorinating a variety of VOCs in the laboratory using palladized iron (Pd—Fe). Halogenated VOCs (HOCs), including trichloroethylene, perchloroethylene, and trichloroethane, have been used for decades as industrial cleaning solutions and general degreasing solvents. Researchers showed that elemental iron (Fe) could be used to dechlorinate many low-molecular-weight chlorinated hydrocarbons. However, Fe alone does not cause complete dechlorination of contaminants and has a prohibitively slow reaction rate for fresh water or air-treatment systems.

This study is to further show the concept that bimetals can produce free radicals efficiently, and thus destroy chemicals, as exemplified with phenol. It is known that the rate constant of the degradation reaction of chemicals is directly related to the surface area of iron. Developing a procedure to make ZVIP with larger surface area can significantly enhance the reactivity and the reaction speed. Promising secondary metals include palladium at low concentrations and lower-cost base metals (e.g., Cu) at greater concentrations. The ability to use secondary metals to increase powder surface area will provide the remediation community a highly reactive metal powder.

6.1 Materials and Methods

Potassium hexachloropalladate ($K_2PdCl_6$) was purchased from Aldrich Chemicals Co. The other reagents were obtained as described above.

To prepare Pd—Fe for the use in this study, iron powder (325 mesh) (10 g) was washed first with 25 mL of 6 M HCl solution for 6 times followed by 25 mL of distilled water for 6 times. Fifteen to 40 mg of $K_2PdCl_6$ were dissolved in 30 to 40 mL of distilled water. This red-orange solution of $K_2PdCl_6$, after added with stirring into the acid-washed iron, turned pale yellow, which indicated the redox occurred.

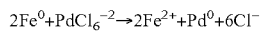

$$2Fe^0 + PdCl_6^{-2} \rightarrow 2Fe^{2+} + Pd^0 + 6Cl^-$$

The Pd—Fe was washed with distilled water (40 mL) for 4 times and used without drying in the experiments. Pd—Fe (0.5 g) was placed in 100 mL of buffer solution containing phenol (100 ppm) in a glass vial. As the vial was being vigorously shaken, oxygen gas was bubbling through the solution. Aliquots of samples were withdrawn with a syringe, and extracted with ethyl acetate (3×20 mL). The combined ethyl acetate extracts were dried over anhydrous sodium sulfate, and then concentrated to an appropriate volume for GC-MS analysis. The GC-MS and other instruments used in this study were the same as those described above.

6.2 Results and Discussion

Figure 16:
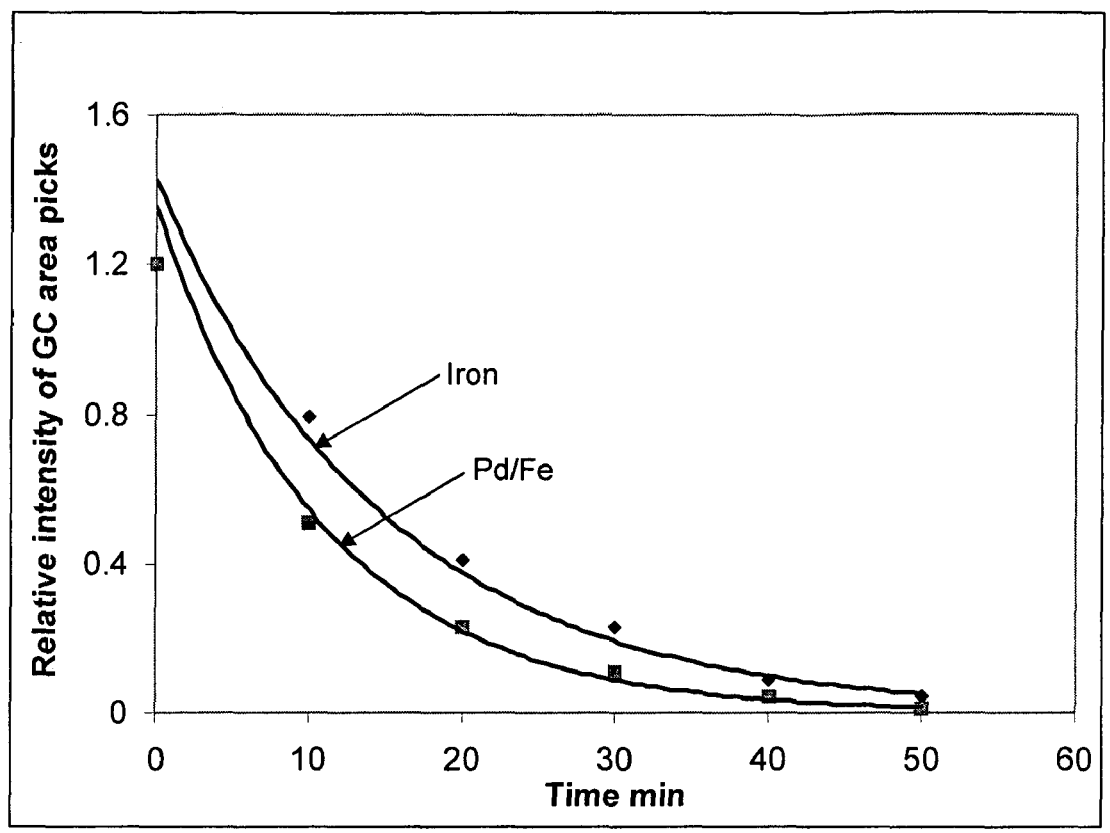
FIG. 16. Disappearance of phenol after treatment with a mixture of microscale palladized iron or microscale iron. The concentrations of phenol were determined with GC-MS. The initial phenol concentration was 100 ppm. The reaction condition is the same as that in FIG. 13.

FIG. 16 shows disappearance of phenol after treatment with a mixture of microscale palladized iron or microscale iron. The concentrations of phenol declined after iron-palladized microparticles were added. Palladized-iron was more efficient than iron itself for complete mineralization (FIG. 16). The half-life of phenol under palladized-iron treatment was approximately 10 min as compared about 17 min under iron treatment.

In summary, the preferred embodiments illustrate rapid generation of hydroxyl free radicals by iron-palladized particles and destruction of, but not limited to, phenol.

Example 7

Degradation of Naphthyl Acetic Acid and Phenanthrene-9 Carboxaldehyde by Free Radicals Generated from Zero Valent Iron ($Fe^0$)

Polycyclic aromatic hydrocarbons (PAHs) represent one of the major classes of hydrophobic organic chemicals found in contaminated soils and sediments. PAHs are known to be biodegradable, and bioremediation is often considered as an option in treating PAH-contaminated soils. In many of the reported studies on biodegradation of PAH in soil, however, removal of PAH has been incomplete, particularly for the high molecular weight compounds. One of the primary factors believed to limit the extent of PAH degradation is the low water solubility of these compounds, which therefore limits their availability to microorganisms that otherwise are able to degrade them.

The preferred embodiments include the use of the free radicals generated by zero valent iron powder (ZVIP) to destroy PAHs. In this study, ZVIP was used to destroy naphthyl acetic acid and phenanthrene-9 carboxaldehyde in aqueous solution at the conditions generating hydroxyl free radicals. These PAHs were chosen as model chemicals in this study because their water solubility is relatively high. In addition, naphthyl acetic acid is a plant growth regulator. The two model chemicals were selected to demonstrate the destruction ability by the free radicals generated from iron powder.

7.1 Materials and Methods

Naphthyl acetic acid and phenanthrene-9-carboxaldehyde were purchased from Aldrich Chemical Co. The sources of the other chemicals were described above.

Iron powder (0.2 g) was added into 50 mL of naphthyl acetic acid or phenanthrene-9-carboxaldehyde (each 100 (g/mL) in buffer, pH=4.8. Oxygen gas was bubbled through the mixture for 30 min. An aliquot of the reaction mixture (20 mL) was extracted with ethyl acetate (3×20 mL). The combined ethyl acetate extracts were dried over anhydrous sodium sulfate, and then concentrated to an appropriate volume for GC-MS analysis. GC-MS and other instruments used to monitor the concentration of phenol was the same as those used in Example 5.

7.2 Results and Discussion

Figure 17:
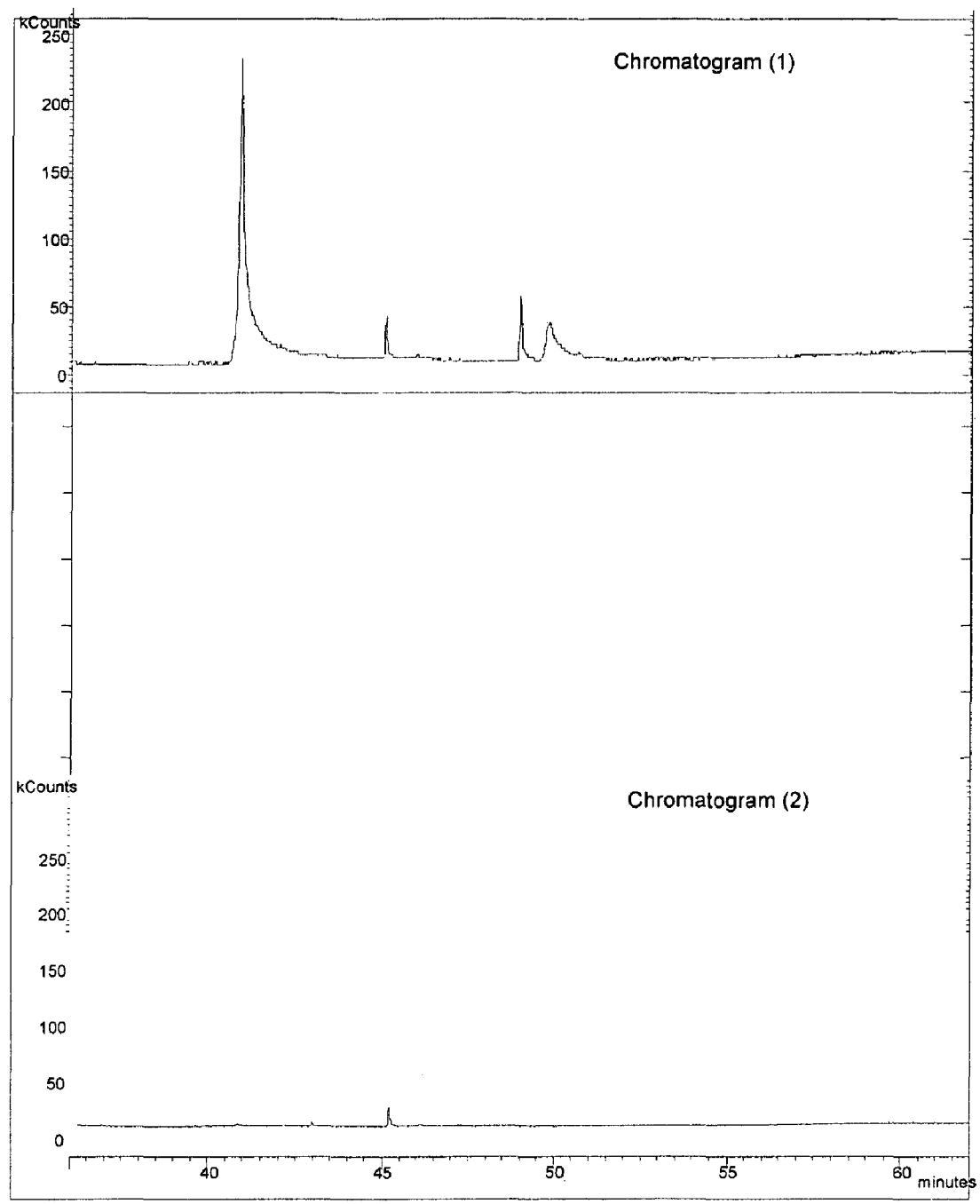
FIG. 17. Degradation of naphthyl acetic acid by microscale iron powder (325 mesh) in buffer solution at pH=4.8 and in presence of oxygen. The reaction condition is the same as that in FIG. 13. Chromatograms shows 100 ppm of naphtyl acetic acid (1) before reaction and (2) after reaction with iron and oxygen.
Figure 18:
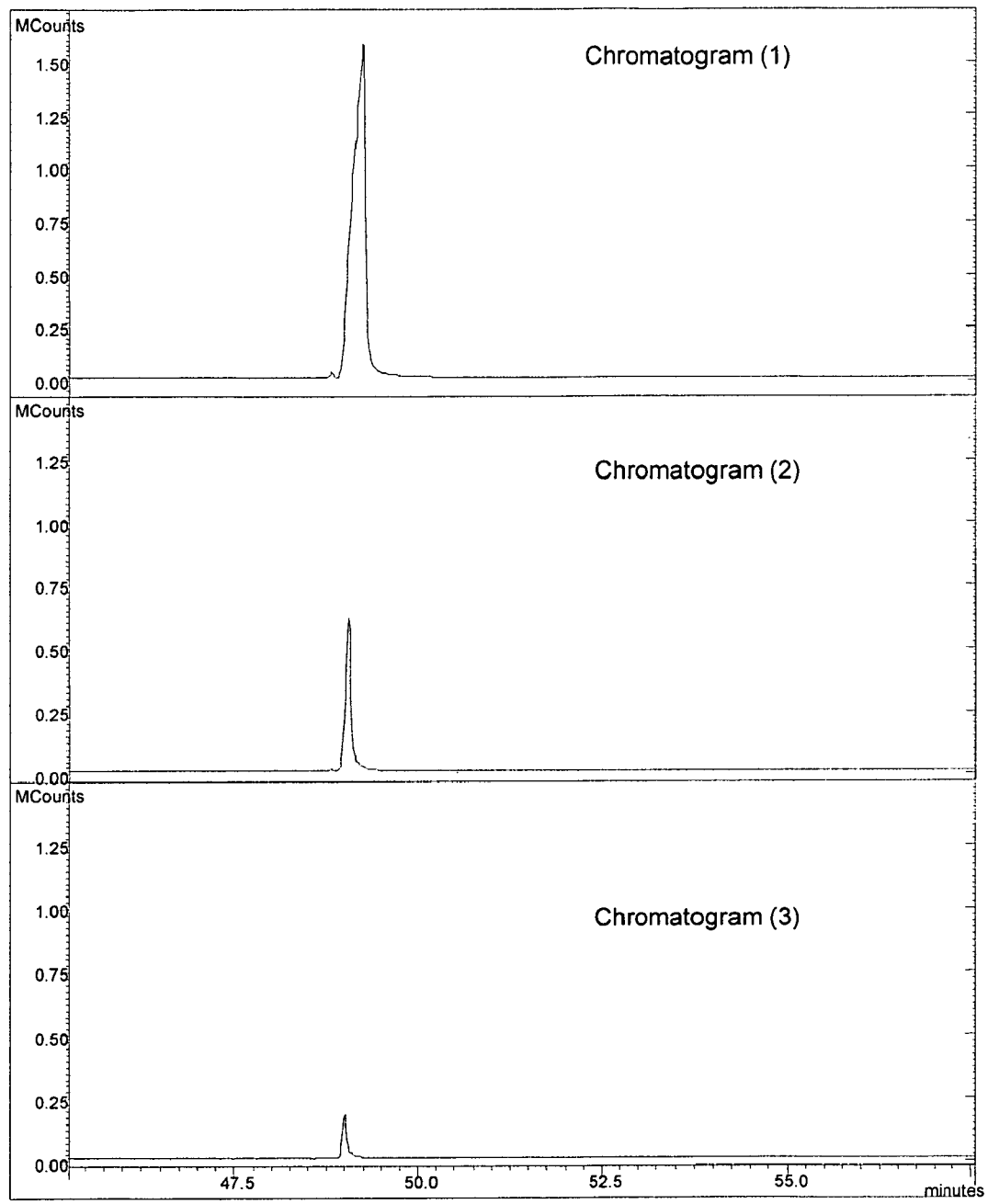
FIG. 18. Degradation of phenanthrene-9 carboxaldehyde by microscale iron powder in buffer solution at pH=4.8. The reaction condition is the same as that in FIG. 13. Chromatograms depicts 100 ppm of phenalthrene-9 carboxaldehyde (1) before reaction, (2) after 10 minutes of reaction and (3) after 30 minutes of reaction with iron.

The two model chemicals were selected to demonstrate the destruction ability by the free radicals generated from iron powder. FIG. 17 shows GC-MS chromatograms of naphthyl acetic acid in the reaction extracts after 30 min of reaction as well as prior reaction. FIG. 18 shows GC-MS chromatograms of phenanthrene-9 carboxaldehyde in the reaction extracts after 30 min of reaction as well as prior reaction. These chromatograms clearly show that naphthyl acetic acid and phenanthrene-9 carboxaldehyde were completely destroyed by free radicals generated from iron powder (FIGS. 17 and 18). The data also demonstrates the potential of using iron powder to completely destruct PAHs and related chemicals.

In summary, complete destruction of PAHs, which are very stable, underlines the extreme high reactivity of hydroxyl free radicals generated from ZVIP, which indicates high application values of ZVIP for various remediation and cleanup purposes.

Example 8

Treatment of Olive Oil Mill Wastewater by Free Radicals Generated by Zero Valent Iron Powder (ZVIP)

Olive oil mills produce liquid waste called olive black water in the olive oil production process. Large volumes of olive oil mill wastewater have been a serious concern of environmental pollution. Biochemical and chemical oxygen demand of this waste may be as high as 100 and 200 g/L, respectively. The organic fraction includes some sugars, tannins, polyphenols, polyalcohols, pectins and lipids (Lamdi et at. 1991). This waste is highly toxic because of its high content of phenolic compounds. Many phenolic and aromatic compounds have been detected in this waste (Lamdi 1993, Sanjust et al. 1991). The dark color is due to phenols (Lamdi et al. 1991). The presence of this waste in rivers decreases the dissolved oxygen content but increases the organic matter and K, Fe, Zn, and Mn contents (Martin et at. 1993, Gharshal 1993). Conventional wastewater treatment methods are relatively ineffective for removing these kinds of pollutants. New methods for the treatment of this wastewater have been developed, in particular, by using microorganisms. White-rot fungi, which produce highly oxidative enzymes such as ligninase, phenol-oxidase and Mn-peroxidase, are able to degrade lignin, phenol, various xenobiotics and environmental pollutants.

The aim of this study was to use the free hydroxyl radicals generated from ZVIP to clean up wastewater effluents from olive oil mills.

8.1 Materials and Methods

Iron powder (0.2 g) was added to 50 mL of olive oil mill wastewater in a 250-mL flask. An equal volume (50 mL) of buffer, pH=4.6 was also added to the flask in order to maintain the same value of pH during the reaction. Oxygen gas was bubbled through the reaction mixture. An aliquot of the reaction mixture (10 mL) was taken and measured with a spectrophotometer.

The spectrophotometer and other instruments used to monitor the reaction was the same as those used in Example 1.

8.2 Results and Conclusion

Figure 19:
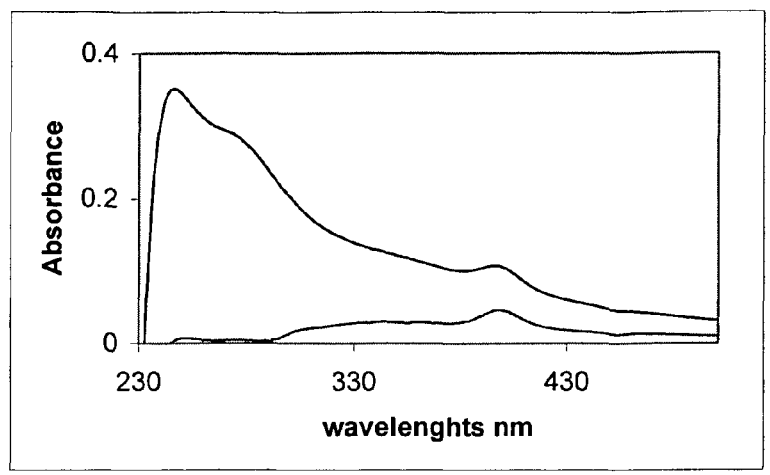
FIG. 19. Evolution of absorption spectra of industrial olive oil liquid waste treated with microscale iron powder in buffer solution. The reaction condition is the same as that in FIG. 13, except that the amount of iron was 2 g/L.
Figure 20:
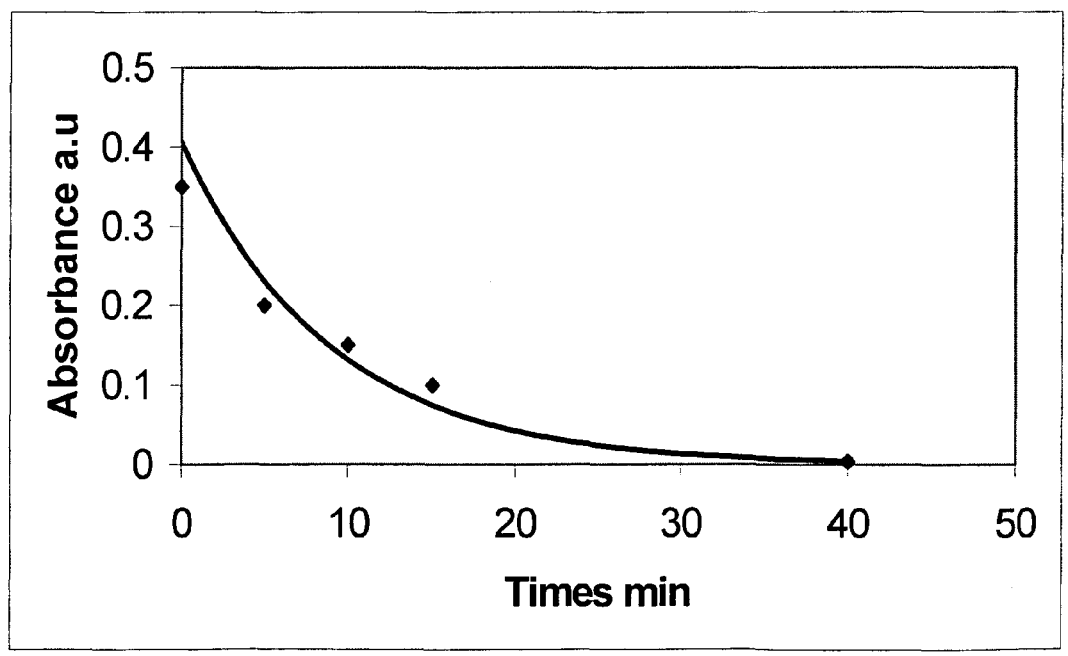
FIG. 20. Industrial olive oil liquid waste destructed with microscale iron powder in buffer solution over reaction time. The reaction condition is the same as that in FIG. 19.

During the reaction between liquid waste and iron, carbon dioxide was detected and a dark precipitation was obtained. After filtration by a sand filter, the filtrate was monitored by a spectrophotometer. FIG. 19 shows the UV-VIS spectra of olive oil mill wastewater before and after the reaction with ZVIP. FIG. 20 shows the kinetics of the reaction. The reaction follows a pseudo-first order model and all the compounds that absorb between 230 nm and 500 nm disappear almost completely after 40 min of reaction.

In summary, free radicals from ZVIP efficiently mineralize wastewater effluents released from olive oil mills. This method is a rapid and inexpensive for the application in the industrial wastewater treatment.

Example 9

Generation of Free Radicals by Nano-Scale Iron and Iron-Nickel Particles

Nanoscale iron particles represent a new generation of environmental remediation technologies that could provide cost effective solutions to some of the most challenging environmental cleanup problems. Iron nanoparticles have large surface areas and high surface reactivity. Equally important they provide enormous flexibility for in situ application. Research has shown that nanoscale iron particles are very effective for the transformation and detoxification of a wide variety of common environmental contaminants such as chlorinated organic solvents, organochlorine pesticide, heavy metals, nitrate and polychlorinated biphenyls (PCBs).

The nanoparticle technology offers great opportunity for both fundamental research and technological application in environmental engineering and science. Nanoscale iron particles are expected to have practical uses in many engineering fields. There are several methods of preparing of nanoscale iron particles. Some of the methods currently used are chemical reduction, sol-gel method, and thermal decomposition. Several methods can be used to produce nanoscale iron:

(a) Chemical reduction method: Nanoscale iron can been prepared by the reaction of $FeCl_3$, and $NaBH_4$ in aqueous solution (Georges et al. 1995). X-ray diffraction, Mossbauer spectroscopy and elemental analyses can be used to confirm the compositions and structure of the product. The reaction can be represented as:

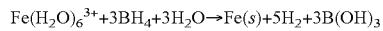

$$Fe(H_2O)_6^{3+} + 3BH_4^- + 3H_2O \rightarrow Fe(s) + 5H_2 + 3B(OH)_3$$

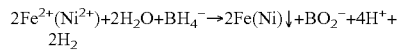

$$2Fe^{2+}(Ni^{2+}) + 2H_2O + BH_4^- \rightarrow 2Fe(Ni)\downarrow + BO_2^- + 4H^+ + 2H_2$$

This approach can also be used to fabricate nanocrystalline Fe—Ni alloy, ultrafine amorphous particles. In addition, it does not require extensive processing equipment and the cost of production can be relatively low compared with other methods.

(b) Sol-gel method: Glass-metal nanocomposites incorporating ultra-fine particles of iron can be prepared by heat treatment of a gel derived from a sol containing silicon tetraethoxide and a metal compound such as $FeCl_3$. In the process, spherical-shaped metal particles are isolated and with diameters ranging from 3-10 nm. The optical absorption and electrical conductance of such films have been measured. The resistivity values in a range of $1 \times 10^{-4}$-$3.9 \times 10^{-3}$ $\Omega$cm have been obtained depending on the particle diameter. The rate of resistivity change increases as the metal particle diameter becomes smaller.

(c) Thermal decomposition: In this method, iron pentacarbonyl can be thermally decomposed in an organic liquid. The mixture is refluxed and stirred for 5-6 h initially at 390 K, then rising to 460 K as the reaction proceed.

9.1 Materials and Methods $Fe(Cl)_3$, $NiCl_2.6H_2O$ and $NaBH_4$ were purchased from Aldrich Chemicals Co. We used the chemical reduction method to prepare nanoscale Fe or Fe—Ni (Georges et al. 1995).

Individual stock solutions were made with each standard phenolic compound at 100 mg/L in buffer, pH=4.8. A volume of 100 mL of this solution was treated by nanoscale Fe or Fe—Ni under bubbling of oxygen gas. Aliquots (10 mL) were sampled to monitor the reaction. Phenol in the control (no Fe or Fe—Ni) and treatment samples was extracted with ethyl acetate following the procedures described in Example 6. The extracts were analyzed with a Varian CP-3800 GC-Saturn 2000 MS. The GC column was ZB-1, 60 m, 0.25 mm i.d., and 0.25 μm film thickness. The oven temperature was programmed from 60° C. (hold for 2 min) to 280° C. at a rate of 4° C./min and then hold for 5 min at 280° C. The injector temperature was 250° C. The injection mode was splitless. The injection volume was 1 μL. The carrier gas was hydrogen at a flow rate of 1 mL/min. MS was operated in El and full scan mode. Solvent delay was 8.5 min. Mass range was 40-250 amu. The trap and transfer line temperatures were 250 and 280° C., respectively.

9.2 Results and Discussion

Figure 21:
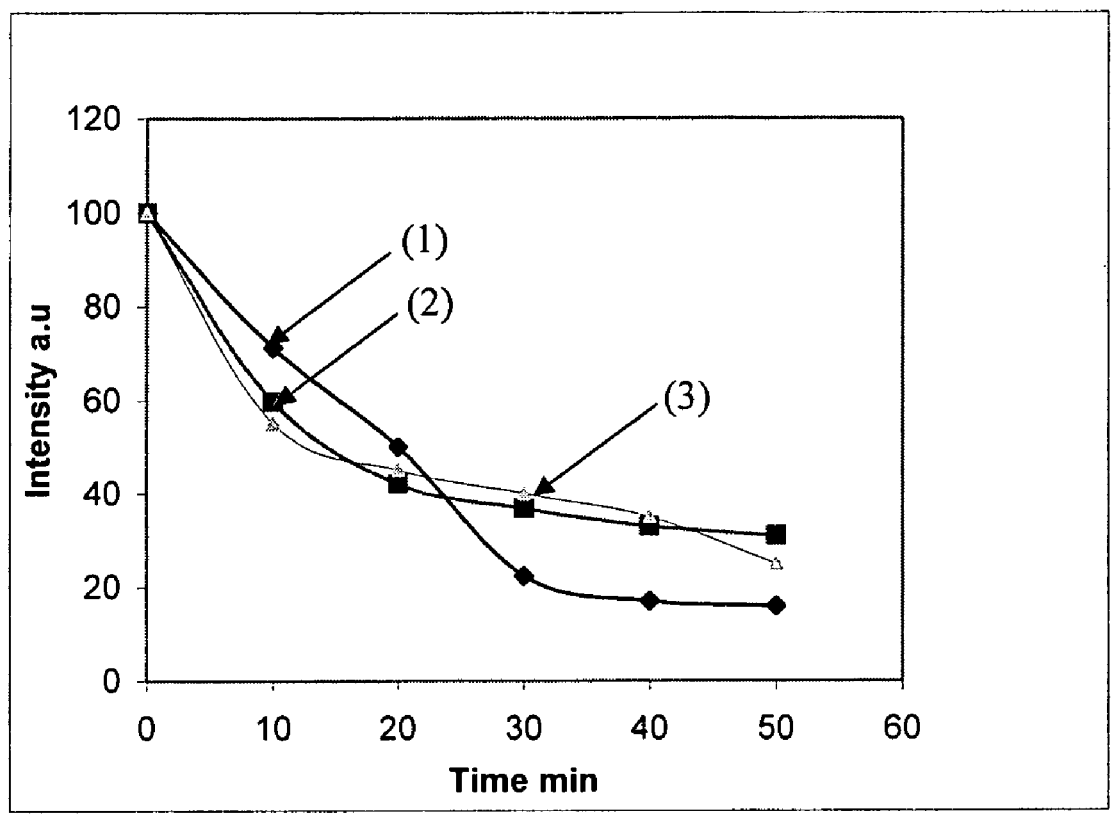
FIG. 21. Degradation of phenol by (1) microscale iron, (2) nanoscale iron and (3) nanoscale iron-nickel in buffer solution. The reaction condition is the same as that in FIG. 13.

Using nanoscale iron in the treatment of water polluted by organic compounds has advantages. It gave a markedly improved reactivity associated with the greater surface area of the nanoscale iron. The beneficial effects of increased surface area per unit weight and increased reaction rates, giving a predicted treatment rate increase of several times to that of conventional granular iron in remediation systems. Treatment of organic chemicals using nanoscale bimetallic particles also offers a rapid means of remediation reaction. The degradation of phenol was monitored by GC/MS. FIG. 21 shows the reaction kinetics for phenol with 325-mesh iron, nanoscale iron and nanoscale Fe—Ni (4:1). Our results show that phenol was decomposed much faster by nanoscale Fe or Fe—Ni than 325-mesh Fe in the first 10 min of reaction. The phenol decomposition rate by nanoscale Fe or Fe—Ni slowed down after 10 min of reaction. The phenol decomposition rate by 325-mesh iron continues to remain fast until 30 min of reaction. For most purposes, use of 325-mesh iron is more economical and feasible than nanoscale metals due to the high cost of nanoscale preparation.

In summary, the results highlight hydroxyl free radical generation from nanoscale Fe and Fe—Ni bimetallic systems, and very quick mineralization of phenol.

Example 10

Disinfection of Water Contaminated by Pathogenic Microorganisms Using Free Radicals Generated by Zero-Valent Iron Powder Free radicals are very active molecules. They can react with practically all chemicals and substances and damage living organisms. After demonstration of a wide range of applications of free radicals generated from ZVIP or bimetals (Examples 1-9 above), the inventors are interested in discovering possible applications of the free radical generation technology for disinfections of microorganisms in various matrices such as river water, waste water, and the like.

Coliform bacteria exist naturally in the intestinal tract of warm-blooded mammals, including humans. Coliform bacteria can also be found in soil, other animals, insects, etc. Wide presence of coliform bacteria and their significance of the environmental pollution problems are main reasons to select them as test organisms in the preferred embodiments. In addition, the total coliform group is relatively easy to culture in the laboratory, and therefore, has been selected as the primary indicator bacteria for the presence of disease causing organism.

Most coliform bacteria are not pathogenic (disease causing) organisms, and are only mildly infectious. For this reason these bacteria are relatively safe to work with in the laboratory. If large numbers of coliforms are found in water, there is a high probability that other pathogenic bacteria or organisms, such as *Giardia* and *Cryptosporidium* may be present.

Typically, bacteria are removed by chemical disinfections, heat sterilization, photoradiation, and/or physical filtration. Filtration alone may not be completely effective, but can improve the performance of disinfectants by removing sediment that can shelter the bacteria. Methods of adding chlorine to water include solution feeders for dry chlorine or liquid chlorine or by feeding gas chlorine directly from 100, 150, or 2000 lb. cylinders. Gas chlorination is recommended only for larger systems that can support the services of a trained water treatment plant operator. Chlorine is normally dosed to a concentration sufficient to maintain a free residual of at least 0.2 parts per million (ppm).

Other disinfectants include iodine, ozone, ultraviolet light, and physical methods such as boiling or steam sterilization. Chlorination is still the most common disinfection method in the United States, although recent concerns have been raised about the reaction of chlorine with organic matter in water. Such a reaction can result in the formation of small organohalogens such as trihalomethanes, which are suspect carcinogenic compounds. For most individual water supply systems, the most common form of treatment is ultraviolet disinfection.

A new method for the disinfection of water and wastewater polluted by bacteria using free radicals generated from ZVIP has been developed.

10.1 Materials and Methods 10.1.1 Nutrient Media

Lactose broth, MacConkey Agar with 0.15% Bile Salts, CV and NaCl, Nutrient Agar, Bile Esculin Agar, iron powder, acetate buffer, oxygen.

10.1.2 Water Samples

Surface river water was collected at Antelias, Beirut, Lebanon. Anteilas is located in a residential area of Beirut and the water is exposed to domestic effluents. All water samples were collected in 2-L autoclaved polycarbonate bottles, and used within 2 h after sampling.

10.1.3 Plating

River water samples were spread on lactose-MacConkey medium and incubated at 37° C. for 48 h to isolate *E. coli* in the river water. White or colorless colonies on the medium were isolated and pure-cultured on lactose-MacConkey medium. This *E. coli* culture at 18-24 h of growth was utilized (without dilution) for the treatment experiments.

A presence-absence method was used to assess if a water sample is contaminated with bacteria. Aliquots of water samples after treatment were spread into nutrient medium (nutrient agar for river water, and lactose-MacConkey agar for *E. coli* culture) and incubated at 37° C. for 24 h.

10.1.4 Presence of Coliforms in River Water

In the presumptive test, the Most Probable Number (MPN) technique was used to enumerate microorganisms, presumably coliforms, in river water. Three replicates and 10-fold dilutions of river water samples in lactose broth with bromcresol purple as acid indicator were prepared. MPN tubes were incubated for 24 h at 37° C. Tubes with gas formation, indicated by displacement of liquid in the insert tube, were counted in each dilution, and the numbers of coliform organisms per milliliter of river water were then calculated by standard procedures (de Man 1975). Another MPN tube containing the same medium and a non-diluted water aliquot was incubated at 44.5° C. for 24 h to identify the fecal conforms. In the confirmed test, cultures that show yellow color and gas production in the presumptive test were transferred onto lactose-MacConkey agar selective for the *coli*-aerogenes group, and incubated for 24 h at 37° C.

10.1.5 Identification of Group D Streptococci in River Water

Bile Esculine Agar (Swan 1954) was utilized for the isolation and identification of group D. *Streptococci* from river water. *Enterococci* and *Streptococci* hydrolyse esculin to esculetin and glucose, which reacts with ferric citrate producing a brownish black precipitate around the colonies.

10.1.6 Water Treatment by Zero-Valent Iron Powder

Twenty-five mL of contaminated water was added to the same volume of a 0.2 M acetate buffer solution at pH 4.8 in a glass vial. Different masses (0.05-0.2 g) of metallic iron powder were added to study the effect of the amount of iron on the sterilization of water. The vials were shaken vigorously and oxygen gas was bubbling in the solution. Aliquots of 3 mL were withdrawn at different times of the reaction to assess the level of bacterial contamination.

10.2 Results and Discussion

The total coliform bacteria test is a primary indicator of "potability", suitability for consumption as drinking water. It measures the concentration of total coliform bacteria associated with the possible presence of disease causing organisms. Two kinds of samples were treated by free radicals, river water and 18-24 h *E. coli* culture.

Table 9 shows the effects of iron mass and treatment time on the sterilization of contaminated water. CFUs decreased dramatically as the amount of iron increased from 0.05 g to 0.2 g. There is no cfu in the plates that were treated with 0.15-0.2 g of iron after 12 min.

TABLE 9

Effects of amount of zero valent iron powder and treatment time on removal of *E. coli* on culture (20 h)[a]

| Iron mass, g | Time reaction | | | |
|---|---|---|---|---|
| | 3 min | 6 min | 9 min | 12 min |
| 0.05 | xxxxx[b] | xxx | xxx | xx |
| 0.1 | xxxx | xx | x | 60 cfu[c] |
| 0.15 | xxx | xx | 25 cfu[c] | 0 cfu[c] |
| 0.2 | xxx | xx | 10 cfu[c] | 0 cfu[c] |

Figure 22:
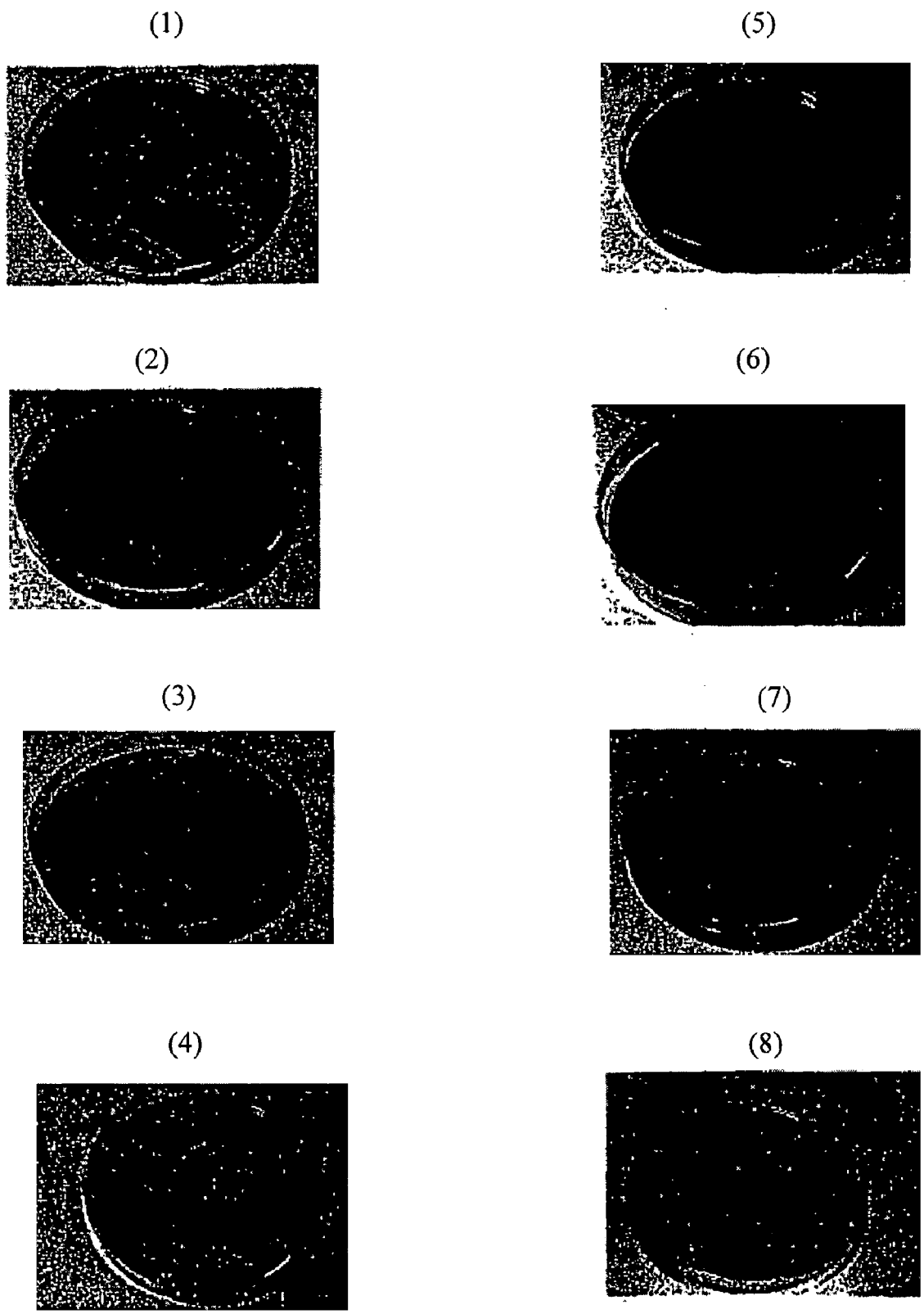
FIG. 22. Generation of free radicals and disinfection of $E.\ coli$. 0.5 µg of $E.\ coli$ solution was introduced into each of plates (1) to (4). This figure shows the $E.\ coli$ growth (1) without treatment of Fe, and after being treated with Fe for (2) 3 minutes, (3) 6 minutes, and (4) 9 minutes. 1 mL of $E.\ coli$ solution was also introduced into each of plates (5) to (8). The figure also shows the $E.\ coli$ growth (5) without treatment of Fe, and after being treated with Fe for (6) 3 minutes, (7) 6 minutes, and (8) 9 minutes.
Figure 23:
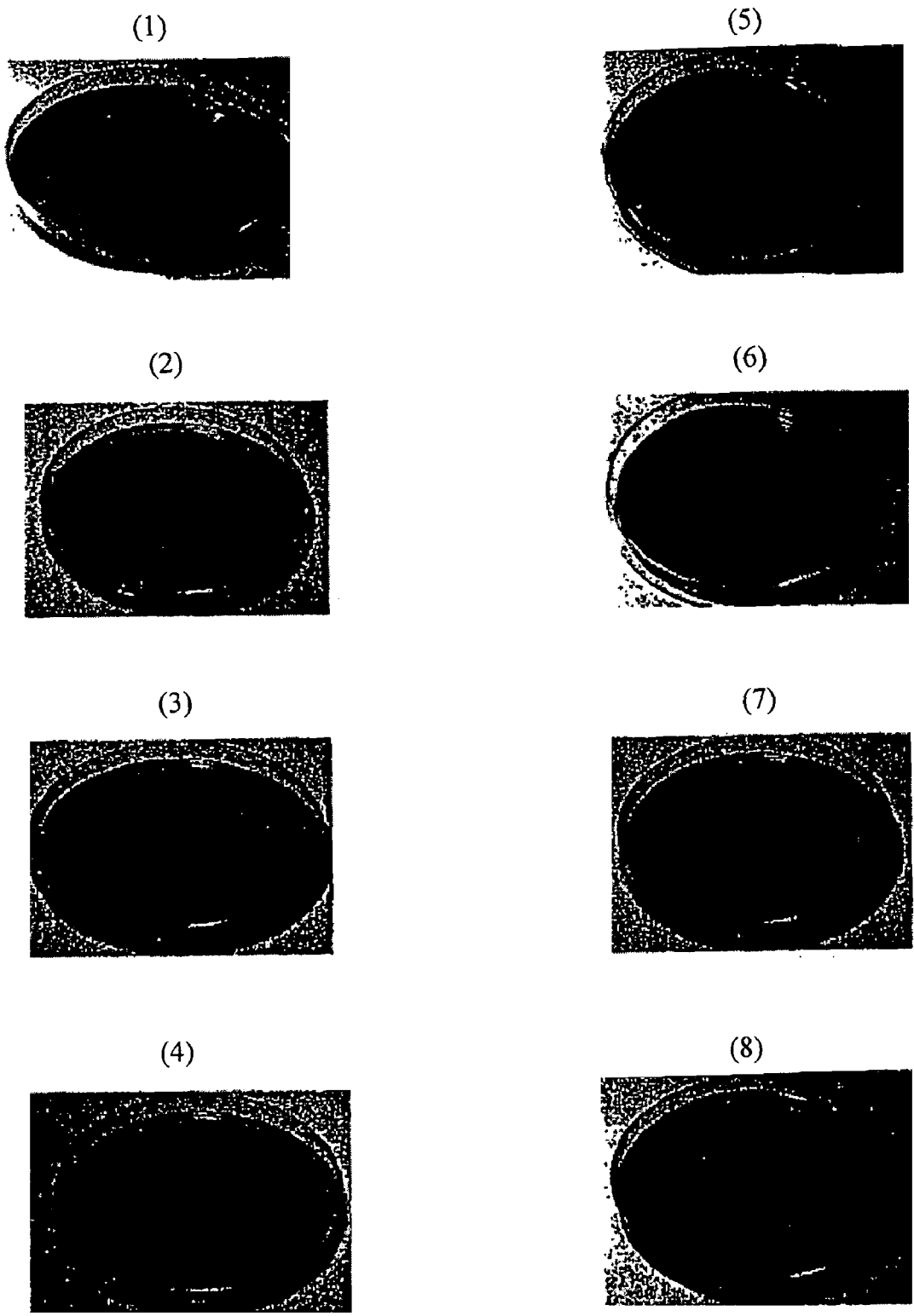
FIG. 23. Generation of free radicals and disinfection of bacteria in river water. 0.5 µg of river water was introduced into each of plates (1) to (4). This figure shows the bacteria growth (1) without treatment of Fe, and after being treated with Fe for (2) 3 minutes, (3) 6 minutes, and (4) 12 minutes. 1 mL of river water was also introduced into each of plates (5) to (8). The figure also shows the bacteria growth (5) without treatment of Fe, and after being treated with Fe for (6) 3 minutes, (7) 6 minutes, and (8) 12 minutes.

[a]Samples were prepared by growing a high quantity of *E. coli*. Each test was done in duplicate.
[b]Highest bacterial growth
[c]0.1 mL of *E. coli* culture spread on the plate FIGS. 22-23 clearly show the efficiencies of bacterial disinfections by iron powder. The results demonstrate that this invented technique can effectively disinfect water contaminated with bacteria.

Two samples were treated in the reaction, a pure 18-24 hour *E. coli* culture and polluted river water collected at a residential area in Beirut. The samples were treated at different conditions of free radical generation (iron mass, reaction time), and analyzed to determine the level of bacterial indicators (total conforms, *E. coli*). Treatment procedure data obtained in the experiments were analyzed to estimate the optimal parameters of complete bacterial destruction under conditions of free radical generation.

In summary, the results exemplify applications of ZVIP (and its combinations with other metals) to disinfect microorganisms, particularly pathogenic bacteria. The technology is applicable for medical sterilization of facilities and supplies, medical waste treatment and all water treatment and management.

Many modifications and variations of the embodiments described herein may be made without departing from the scope, as is apparent to those skilled in the art. The specific embodiments described herein are offered by way of example only.

LITERATURE CITED

The following references cited herein are each incorporated by reference.

Alfaro, G.; Meuens, M.; Birth, G. S. Liquid Analysis by Dry-Extract Near-Infrared Reflectance on Fiberglass (1990) Appl. Spectrosc. 44:979-986

Aray, S.; Mahajan, M. Colorimetric Determination of Ascorbic Acid in Pharmaceutical Preparations and Biological Samples. Mikrochim. Acta 1997, 127(1-2), 45

Aruoma, O. I. In: "Free Radicals in Topical Diseases" (O. I. Aruoma, Ed) Chapter 11. Harwood Academic publ; London, 1993.

Barbeni, M.; Minero, C.; Plizzetti, E.; Borgarello, E.; Serpone, N. (1987) Chemical degradation of chlorophenols with Fenton's reagent. Chempsphere 16:22-25.

Bowers, A. R.; Eckenfelder, W. W.; Gaddipati, P.; Mosen, R. M. (1989) Treatment of toxic or refractory wastewater with hydrogen peroxide. Water Sci. Technol. 21:447.

Cabrera. F.; Toca, G. C.; Diaz, E.; Arambari, D. E. P. (1984) Acidmine-water and agricultural pollution in river skirting the Donana national park. Water Res. 18(12):1469-1482

Cheesmen, K. H.; Slater T. F. (1993) An introduction to free radical biochemistry. Br. Med. Bull. 49:481-493.

Cheng, I. F.; Fernando, Q.; Korte, N. (1997) Electrochemical dechlorination of 4-chlorohenol to phenol. Environ. Sci. Technol. 31:1074-1078.

Cheng, A. Q. F.; Naradoun, C.; Morales, J.; Hutsheson, R. (2002) Hydrogenation of phenol by Pd/Mg and Pd/Fe bimetallic systems under mild reactions conditions. Industrial & Engineering Chemistry Research 41:3071-3074.

Cláudio Roberto Lima de Souza; Patrício Peralta-Zamora (2005) Degradation of reactive dyes by the metallic iron/ hydrogen peroxide system. Quím. Nova vol. 28 no. 2 Sao Paulo March/April.

Deutsch, J. C.; Kolhouse, J. F. (1993) Ascorbate and dehydroascorbate measurement in aqueous solutions and plasma determined by gaschromatography-mass spectrometry. Anal Chem. 65:321-326.

Deutsch, J. C.; Santhosh-Kumar, C. R.; Hassell, K. L.; Kolhouse, J. F. (1994) Variation ion in ascorbic acid oxidation routes in $H_2O_2$ and cupric ion solution as determined by GC/MS. Anal Chem. 66:345-350.

Deutsch, M. O.; Weeks, C. E. (1965) Microfluorometric assay for vitamin C J. Assoc. Off. Anal. Chem. 48:1248-1256.

Dong, C. Destruction of Hazardous Organic Contaminants by Advanced Oxidation Processes, PhD Dissertation, University of Delaware, Newark, Del., 1993, p. 232.

Fresenieus J. Anal. Chem. 357:1174.

Frei, B; England, L; Ames, B. N. (1989) Proc. Natl. Acad. Sci. USA 86:6377.

Fridovich I. (1983) Superoxide radical, an endogeneous toxicant. Ann. Rev. Pharmacol. Toxicol. 23:239-257.

Ghauch, A.; Rima, J.; Martin-Bouyer, M. (2001). Reductive degradation of carbaryl in water by zero-valent iron. Chemosphere 42:419-424.

Gharshall, N. (1993) Production of single cell protein from olive oil mill wastewater by yeasts. Environmental Technology 14:391-395.

Giangiacomo, R.; Dull, G. G. (1986). Determination of Individual simple sugars in aqueous solution by near infrared spectrophotometry J. Food Sci. 51:679-683.

Gillham, R. W. (1993) Cleaning halogenated contaminants from groundwater. U.S. Pat. No. 5,266.

Greenberg, R. S.; Andrews, T.; Kakarla, P. K. C.; Watts, R. J. In-situ Fenton-like oxidation of volatile organics: laboratory, pilot and full-scale demonstrations, 1997 Extended Abstracts for the ACS Special Symposium on Emerging Technologies in Hazardous Waste Management IX, September. 15-17, Pittsburgh, Pa., 1997, p. 219.

Gu, M. J.; Dickey, X.; Yin, L. L. Removal of chlorinated organic compounds and radionuclides from contaminated groundwater by zero-valent iron, 1997 Extended Abstracts for the ACS Special Symposium on Emerging Technologies in Hazardous Waste Management IX, September. 15-17, Pittsburgh, Pa., 1997, p. 53.

Gutteridge, J. M. C. (1984) Reactivity of hydroxyl and hydroxyl-like radical discriminated by release of thiobarbituric-acid-reactive material from deoxyribose, nucleosides and benzoate. Biochemical J. 243:803-808.

Halliwell, B. Free radicals, oxygen toxicity and aging. In: Age pigments. R. S. Sohal (Ed.); Elsevier, Amsterdam. 1981.

Hodge, J. E. Origin of Flavor in Foods, Nonenzymatic Browing Reaction. In: Symposium on Foods; the Chemistry and Physiology of Flavors. Schultz, H. W; Day, E. A.; Libbey, L. M. (Eds.); AVI publishing Co., Westport, Conn., 1967, pp 465-491.

Hall, A. K.; Harrowfield, J. M., Hart, R. J. and McCormick, P. G. (1996) Mechanochemical reaction of DDT with calcium oxide. Environ. Sci. Technol. 30:3401-3407.

Horwitz, W. Official Methods of Analysis of the Association of Official Analytical Chemists, 5th ed.; Association of Official Analytical Chemists, Arlington, Va., 1990.

Kishida, E.; Nishimoto, -Y.; Kojo, S. (1992) SpecificDetermination of ascorbic acid with chemical derivatization and high-performance Anal. Chem. 64:1505

Kissinger, P. T A.; Pachla. L. (1987) Determination of ascorbic acid and dehydroascorbic acid using liquid chromatography with ultraviolet Food Technol. 41:108.

Kosugi, H.; Kato, T.; Kikugawa, K. (1987) Formation of yellow, orange, and red pigments in the reaction of alk-2-enals with 2-thiobarbituric acid. Anal. Biochem. 165:456-464.

Kim H J. Determination of total vitamin C by ion exclusion chromatography with electrochemical detection J Assoc off Anal Chem. 1989 July-August, 72(4): 681-6

Kunsst, A.; Draeger, B.; Ziegenhom, J. In: Methods in Enzymatic Analysis 2. H. U. Bergmeyer (Ed.); 3rd Ed. Academic Press, New York. 1984. pp. 163-172.

Lamdi, M. (1993) Future prospect and constants of the olive mill wastewater use and treatment: A Review, Bioprocess Engineering 8:209-214.

Lamdi, M.; Kandir, A.; Garcia, L. J. (1991) The use of *Aspengillus niger* for the bioconversion of olive mill wastewater. Applied Microbiol. 34:828-831.

Lanza, E.; Li, B. W. (1984) Application for near infrared spectroscopy for predicting the sugar content of fruit juices J. Food Sci. 49:995-998.

Lau, O. W.; Luk, S. F.; Wong, S. (1986) Spectrophotometric determination of ascorbic acid in canned fruit juices, cordials, and soft drinks Analyst 111:665-670.

Li, W.; Goovaerts, P.; Meurens, M. (1996) Quantitative analysis of individual sugars and acids in orange juices by near-infrared spectroscopy J. Agric. Food Chem. 44:2252-2259.

Lobry, C. A. de Bruy-Alberda; van Ekenstein, W. A. (1899) Isomerization of carbohydrates in alkaline media, considered to embrace both epimerization of aldoses and ketoses and aldose-ketose interconversion. Rec. Tray. Chim. 14:150

Matheson, L. J.; Tratnyek, P. G. (1994) Reductive dehalogenation of chlorinated methanes by iron metal. Environ. Sci. Technol. 28:2045-2053.

Martin, A.; Borja, R.; Chica, A. (1993) Kinetic study of an anaerobic fluidized bed system used for the pollution of fermented olive oil wastewater. J. Chem. tech. Biotechnol. 56:155-162

Martin-Fernandez, M. L.; Tobin, M. J.; Clarke, D. T.; Gregory, C. M.; Jones, G. R. (1998) Subnanosecond polarized microfluorimetry in the time domain: An instrument for studying receptor trafficking in live cells. Review of Scientific Instruments 69:540-543.

Mukhodhyay; C. K; Chatterjee, I. B. (1994a) NADPH-initiated cytochrome P450-mediated free metal ion-independent oxidative damage of microsomal proteins. Exclusive prevention by ascorbic acid J. Biol. Chem. 269:30200

Mukhodhyay, C. K.; Chatterjee, I. B. (1994b) Ascorbic acid prevents lipid peroxidation and oxidative damage of proteins in guinea pig extrahepatic tissue microsomes J. Biol. Chem. 269:13390 sMcClure, W. F.; Maeda, H.; Dong, J.; Liu, Y.; Ozaki, Y. (1996) Two-Dimensional Correlation of Fourier Transform Near-Infrared and Fourier Transform Raman Spectra I: Mixtures of Sugar and Protein Appl. Spectrosc. 50:467-475

Organic Chemistry Data Booklet, August 2001. Thermodynamic data, Geneva, Switzerland.

Pachla L. A.; Reynolds, D. L.; Kissinger, P. T. (1985) Analytical methods for determining ascorbic acid in biologica samples, food products, and pharmaceuticals J. Assoc. Off. Anal. Chem. 68:72.

Palmer, P. L. Reactive Walls. In: E. K. Nyer et al. (Eds.), In Situ Treatment Technology. CRC Press, Boca Raton, Fla., 1996, pp. 271-288.

Prodolliet, J.; Hischenhuber, C. (1998) Standardisation of the detection of invert sugar addition to apple juice by capillary gas Z. Lebensm. Unters Forsch. A 207:345-350.

Pryor, W. A.; Godber, B. L. J. (1991) Free Radical in Biology, New York, N.Y. Academic Press 54:381-387. (Handbook)

Rima, J.; Ghauch, A.; Martin-Bouyer, M. (1999) Rapid treatment of water contaminated inated with atraizine and parathion with zero-valent iron. Chemosphesphere 3:1309-1315.

Sanjust, E.; Pompei, R.; Resiciggno, A.; Augusto, R.; Ballero, M. (1991) Olive milling wastewater as a medium for growth of four *pleurotus* species. Appl. Biochem. Biotechnol. 31:223-235.

Savles, G. D.; You, G. R.; Wang, M. X. (1997) DDT, ODD and DDE dechlorination by zero-valent iron. Environ. Sci. Technol. 31:3448-3454.

Sweeny, k. H. 1981a "The reductive Treatment of industrial wastwaters: I. Process Description". In G. F. Bennett 9 Ed), Americain institute of Chemical Engineers, Symposium Series, Water-1980, 77 (209), 67-71, 72-88.

Sweeny, K. H. 1983b. Treatment of reductible Halohydrocarbons containing Aqueous Stream. U.S. Pat. No. 4,382,865.

Senzaki, T.; Kumagai, Y. (1988) Removal of chlorinated organic compounds from wastewater by reduction process: treatment of 1,1,2,2-tetrachloroethane with iron powder. Kogyo Yosui 357:2-7.

Sergio L. C. Ferreira, Marcus L. S. F. Bandeira, Valfredo A. Lemos, Hilda C. dos Santos, A. C. Spinola Costa, Djane S. de Jesus (1997) Sensitive spectrophotometric determination of ascorbic acid in fruit juices and pharmaceutical formulations using 2-(5-bromo-2-pyridylazo)-5-diethylaminophenol (Br-PADAP)

Senzaki, T.; Kumagai, Y. (1989) Removal of chlorinated organic compounds from wastewater by reduction process: treatment of trichloroethylene with iron powder. Kogyo Yosui 369:19-25.

Senzaki T.; Kumagai, Y. (1991) Removal of chlorinated organic compounds from wastewater by reduction process: treatment of trichloroethylene with iron powder. Kogyo Yosui 391:29-35.

Slater, T. F. (1984) Free-radical mechanisms in tissue injury. Biochem. J. 222:1-15.

Sultan, S. M.; Abdennabi, A. M.; Suliman, F. E. O. (1994) Flow injection colorimetric method for the assay of vitamin C in drug formulations Talanta 41:125-130

Sweeney, K.; Fischer, J. R. (1972) Reductive degradation of halogenated pesticides U.S. Pat. No. 3,640,821, Feb. 8, 1972.

Sweeney, K.-I. (1981) The reductive of industrial wastewater: Process description In: G. F Bennett (Ed.), American institute of Chemical Engineers, Symposium Series, Water-1980, 77 (209): 67-71.

Trifiro, A.; Saccani, G.; Gherardi, S.; Vicini, E.; Spotti, E.; Previdi, M. P.; Ndagijimana, M.; Cavalli, S.; Reschiotto, C. (1997) Use of ion chromatography for monitoring microbial spoilage in the fruit juice industry J. Chromatogr. A 770:243-252.

Tyre, B. W.; Watts, R. J.; Miller, G. C. (1991) Treatment of four biorefractory contaminants in soils using catalyzed hydrogen peroxide. J. Environ. Qual. 20:832.

Vogel, T. M.; Gridlle, C. S.; McCarty, P. L. (1987) Transformations of halogenated aliphatic compounds. Environ. Sci. Technol. 21:722-736.

Weast, R. C. (1984) CRC Handbook of Chemistry and Physics, 64 Ed., CRC Press, Inc., Boca Raton, Fla., USA.

Watts, R. J.; Udell, M. D.; Rauch, P. A.; Leung, S. W. (1990) Treatment of pentachlorophenol-contaminated soils using Fenton's reagents. Haz. Waste Haz. Mater. 7:335.

Warner, S. D.; Szerdy, F. K.; Yamane, C. L. Permeable Reactive Treatment Zones: A Technology Update. In: Contaminated Soils. E. J. Calabrese, P. T. Kostecki, M. Bonazountas (Eds). Amherst Scientific Publisher, Amherst, Mass. 1998. p. 315.

Yang, G. C. C. Remedaition of Organic Contaminated Sites by Fenton Process (11), Final Report, R.O.C. NSC 87-2621-P-110-005. 1999. pp. 264.

Yang, G. C. C.; Lai, W. H. (1997) Chemical oxidation treatment of phenol-contaminated soil by Fenton process. Extended Abstracts for the ACS Special, Symposium on Emerging Technologies in Hazardous Waste Management IX, Sep. 15-17, 1997. Pittsburgh, Pa., USA. p. 107.

Yang, G. C. C.; Long, Y. W. (1998) Treatment of phenol-contaminated soil by electrokinetics-Fenton process, Book of Abstracts-I and EC Paper 056, 216th ACS National Meeting, Aug. 23-27, 1998. Boston, Mass., USA.

What is claimed is:

1. A method for the disinfection of water polluted by microorganisms and organic compounds comprising adding a zero-valent iron to the water, adding oxygen to the water, and maintaining the water at a pH of about 2 to 5.5, thereby generating hydroxyl free radicals which cause oxidative destruction that leads to mineralization of said organic compounds, cell death or bacterial death, resulting in the disinfection of water.

2. The method of claim 1, wherein at least a portion of the zero-valent iron is a bimetallic compound with zinc, nickel, or palladium.

3. The method of claim 1, wherein zero-valent iron is at a concentration of about 0.01 g/L to 10 g/L.

4. The method of claim 1, wherein the water is selected from the group consisting of river water, wastewater, groundwater, swimming pools, domestic wastewater, industrial effluents, hospital liquid wastes, petroleum liquid wastes, industrial olive oil effluents, food industrial effluents, paper industrial effluents and contaminated soil treatment.

5. The method of claim 1, wherein the microorganisms comprise bacterium.

6. The method of claim 5, wherein the bacteria are pathogenic.

7. The method of claim 1, wherein the microorganisms are selected from the group consisting of Enterobacteria, staphylococci, streptococci, fungi, and protozoa.

8. The method of claim 1, wherein adding oxygen to the water comprises pumping oxygen gas or air into the water.

9. The method of claim 8, wherein oxygen gas or air is pumped into the water at 0.1 to 15 liters/min.

10. The method of claim 1, wherein the organic compounds are selected from the group consisting of pesticides, PCB's, PAHs, organochlorines, organophosphates, and phenolic compounds.

11. The method of claim 1, wherein the water is selected from the group consisting of river water, wastewater, groundwater, swimming pools, domestic wastewater, industrial effluents, hospital liquid waste, petroleum liquid waste, and industrial olive oil effluents.

12. A method of disinfecting water polluted by microorganisms and organic compounds comprising:

adding zero-valent iron and oxygen to the water at a pH of about 2 to 5.5 in order to generate hydroxyl free radicals as represented by the chemical equation:

$$Fe^0+O_2+2H^+ \rightarrow Fe^{2+}+H_2O_2 \rightarrow Fe^{3+}+OH+OH^-$$

wherein the hydroxyl free radicals react with organic compounds, via oxidative destruction, leading to the mineralization of said organic compounds, cell death or bacterial death, which results in the disinfection of the water.

* * * * *